US011999781B2

(12) United States Patent
Furrer et al.

(10) Patent No.: US 11,999,781 B2
(45) Date of Patent: Jun. 4, 2024

(54) ANTIBODY VARIANTS

(71) Applicant: Tillotts Pharma AG, Rheinfelden (CH)

(72) Inventors: Esther Maria Furrer, Rheinfelden (CH); Stian Foss, Oslo (NO); Jan Terje Andersen, Oslo (NO); Inger Sandlie, Oslo (NO)

(73) Assignee: Tillotts Pharma AG, Rheinfelden (CH)

( * ) Notice: Subject to any disclaimer, the term of this patent is extended or adjusted under 35 U.S.C. 154(b) by 0 days.

(21) Appl. No.: 16/648,537

(22) PCT Filed: Sep. 11, 2018

(86) PCT No.: PCT/EP2018/074522
§ 371 (c)(1),
(2) Date: Mar. 18, 2020

(87) PCT Pub. No.: WO2019/057564
PCT Pub. Date: Mar. 8, 2019

(65) Prior Publication Data
US 2020/0216527 A1 Jul. 9, 2020

(30) Foreign Application Priority Data

Sep. 19, 2017 (EP) .................................... 17191989

(51) Int. Cl.
*C07K 16/24* (2006.01)
(52) U.S. Cl.
CPC ........ *C07K 16/241* (2013.01); *C07K 2317/41* (2013.01); *C07K 2317/72* (2013.01); *C07K 2317/732* (2013.01); *C07K 2317/734* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| 7,645,450 | B2 * | 1/2010 | Yoo ......................... | A61P 19/02 424/133.1 |
| 11,319,383 | B2 * | 5/2022 | Andersen ................ | C07K 16/22 |
| 11,459,383 | B2 * | 10/2022 | Gunde .................... | A61P 29/00 |

FOREIGN PATENT DOCUMENTS

| KR | 10-2016-0142849 | | 12/2016 | |
| KR | 10-2018-0127320 | | 11/2018 | |
| WO | 2017/158426 | A1 | 9/2017 | |
| WO | WO 2017/158092 | * | 9/2017 | |
| WO | WO-2017158426 | A1 * | 9/2017 | ............. C07K 16/00 |

OTHER PUBLICATIONS

Steidl et al. "In vitro affinity maturation of human GM-CSF antibodies by targeted CDR-diversification". Molecular Immunology 46 (2008) 135-144. (Year: 2008).*

Natsume et al. "Improving effector functions of antibodies for cancer treatment: Enhancing ADCC and CDC". Drug Design, Development and Therapy 2009:3 7-16 (Year: 2009).*
Wang et al. "Monoclonal Antibodies with Identical Fc Sequences Can Bind to FcRn Differentially with Pharmacokinetic Consequences". Drug Metabolism and Disposition Sep. 2011, 39 (9) 1469-1477. (Year: 2011).*
Jaramillo et al. "Toward in vitro-to-in vivo translation of monoclonal antibody pharmacokinetics: Application of a neonatal Fc receptor-mediated transcytosis assay to understand the interplaying clearance". MABS 2017, vol. 9, No. 5, 781-791 [ published online May 25, 2017] (Year: 2017).*
Wang and Lin. "Tumor necrosis factor and cancer, buddies or foes?" Acta Pharmacol Sin. Nov. 2008; 29(11): 1275-1288. (Year: 2008).*
Rong Deng et al., "Pharmacokinetics of Humanized Monoclonal Anti-Tumor Necrosis Factor-alpha Antibody and its Neonatal Fc Receptor Variants in Mice and Cynomolgus Monkeys", *Drug Metabolism and Disposition*, vol. 38, No. 4, pp. 600-605 (Apr. 1, 2010).
Yik Andy Yeung et al., "Engineering Human IgG1 Affinity to Human Neonatal Fc Receptor; Impact of Affinity Improvement on Pharmacokinetics in Primates", *Journal of Immunology*, vol. 182, No. 12, pp. 7663-7671 (Jun. 1, 2009).
Timothy Kuo et al., "Neonatal Fc receptor and IgG-based therapeutics", *MABS*, vol. 3, No. 5, pp. 422-430 (Sep. 1, 2011).
Takuo Suzuki et al., "Importance of Neonatal FcR in Regulating the Serum Half-Life of Therapeutic Proteins Containing the Fc Domain of Human IgG1: A Comparative Study of the Affinity of Monoclonal Antibodies and Fc-Fusion Proteins to Human Neonatal FcR", *Journal of Immunology*, vol. 184, No. 4, pp. 1968-1976 (Feb. 12, 2010).
Yasmina Noubia Abdiche et al., "The Neonatal Fc Receptor (FcRn) Binds Independently to Both Sites of the IgG homodimer with Identical Affinity", *MABS*, vol. 7, No. 2, pp. 331-343 (Mar. 4, 2015).
Sally E. Ward et al., "Targeting FcRn for the Modulation of Antibody Dynamics", *Molecular Immunology*, vol. 67, No. 2, pp. 131-141 (Mar. 9, 2015).
Arvind Rajpal et al., "Introduction: Antibody Structure and Function", *Therapeutic Fc-Fusion Proteins*, First Edition, Ed. Steven Chamow et al., Wiley-VCH Verlag GmbH & Co. KGaA, Weinhein, Germany, pp. 1-44 (Feb. 19, 2014).
Paolo Biancheri et al., "Proteolytic Cleavage and Loss of Function of Biologic Agents that Neutralize Tumor Necrosis Factor in the Mucosa of Patients with Inflammatory Bowel Disease", *Gastroenterology*, vol. 149, No. 6, pp. 1564-1574 (Jul. 11, 2015).
Michelle Kinder et al., "Engineered Protease-resistant Antibodies with Selectable Cell-killing Functions", *Journal of Biological Chemistry*, vol. 288, No. 43, pp. 30843-30854 (Oct. 25, 2013).
Shields et al. "High Resolution Mapping of the Binding Site on Human IgG1 for FcγRI, FcγRII, FcγRIII, and FcRn and Design of IgG1 Variants with Improved Binding to the FcγR". The Journal of Biological Chemistry, vol. 276, No. 9, Issue of Mar. 2, pp. 6591-6604. 2001. (Year: 2001).

* cited by examiner

Primary Examiner — Marianne P Allen
(74) Attorney, Agent, or Firm — Smith Patent, LLC; Chalin A. Smith

(57) ABSTRACT

The present invention relates to antibodies which bind to TNFα and exhibit modified FcRn-binding. The antibodies of the invention have good effector functions and/or pharmacokinetic properties.

5 Claims, 5 Drawing Sheets
Specification includes a Sequence Listing.

ANTIBODY VARIANTS

PRIORITY

This application corresponds to the U.S. National phase of International Application No. PCT/EP2018/074522, filed Sep. 11, 2018, which, in turn, claims priority to European Patent Application No. 17.191989.7 filed Sep. 19, 2017, the contents of which are incorporated by reference herein in their entirety.

SEQUENCE LISTING

This application contains a Sequence Listing that has been submitted in ASCII format via EFS-Web and is hereby incorporated by reference in its entirety. Said ASCII copy, created on Mar. 18, 2020, is named LNK_215US_SEQ_LISTING.txt and is 28,878 bytes in size.

FIELD OF THE INVENTION

The present invention relates to modified antibodies having altered effector functions and/or altered pharmacokinetic properties. The antibodies are useful in the therapeutic treatment of various disorders, in particular of inflammatory conditions.

BACKGROUND

Monoclonal antibodies have gained increasing importance as therapeutic reagents in clinical medicine over the last 20 years. For many years, efforts to improve antibodies concentrated on reducing their potential immunogenicity, leading to humanized or even fully human antibodies. Another approach aims to optimize antibodies by improving their effector functions. While direct effects are mediated by the variable antigen binding region of the antibody, indirect effects are mediated by the constant Fc region. Efforts to improve effector functions mainly concentrate on modulating the Fc region. In addition, improving the serum half-life of therapeutic antibodies is desirable, which may reduce the amount of required antibodies, and may increase their convenience for patients by prolonging treatment intervals.

For therapeutic applications, immunoglobulin G (IgG) has been the preferred class of choice for several reasons; IgGs are easy to purify, are relatively stable on storage, can be administered intravenously, have extended biological half-life in vivo and are able to engage a range of biological effector functions such as activation of complement dependent cytotoxicity (CDC) and recruitment of effector cells through various Fc-receptor interactions (antibody-dependent cellular cytotoxicity; ADCC). Of the five immunoglobulin classes, IgG exhibits the longest biological half-life due to its unique interaction with the IgG recycling receptor, the neonatal Fc receptor (FcRn). One of the known functions of the receptor is to rescue IgG from catalytic degradation. A solved FcRn-Fc cocrystal structure has shown that the interaction with Fc occurs in the IgG hinge-$C_H2$-$C_H3$ region. This interaction occurs in a strictly pH-dependent manner at acidic pH of 6.0-6.5 in the endosomes. Bound IgG molecules are recycled back to the cell surface where they are released at physiological pH of 7.4 into the circulation, whereas noncomplexed IgG molecules are destined for lysosomal degradation. This recycling is the mechanism for the extended half-life of IgG; modulation of the FcRn-IgG interaction will therefore allow specific control of the serum half-lives of gamma immunoglobulins and Fc-fusion proteins.

Depending on the application it may be desirable to increase or reduce the serum residence time of IgG. For therapeutic application a longer half-life is desirable as smaller doses and fewer injections will be required. Several approaches to increase the half-life have been investigated including the use of polyethylene glycol (PEG), generation of albumin- or Fc-fusion proteins and strengthening the FcRn-IgG interaction. PEGylated pharmaceuticals have been in the clinic since 1990 and PEGylation is an established technology for extension of drug residence in the blood. Since human serum albumin (HSA) is also recycled by FcRn via a pH-dependent interaction, several albumin-fusion proteins to enhance stability and half-life have also been produced. Additionally, antibody fragments fused to albumin or albumin-binding domains have demonstrated prolonged serum residence time in preclinical studies. The generation of Fc-fusion proteins is another strategy that will endow proteins or peptides with properties similar to an intact antibody.

Modifications of the Fc region that have been investigated are summarized in Saxena (2016) Frontiers in Immunology, Vol. 7, Article 580.

There is an ongoing need for antibodies having improved effector functions and/or pharmacokinetics.

SUMMARY OF THE INVENTION

The inventors of this application found that certain specific mutations in the Fc region of an antibody dramatically increase the antibody's affinity to FcRn at pH 6, whereas the affinity at pH 7.4 remains low. Antibodies having the mutations are expected to have improved pharmacokinetic properties. In addition, the antibodies exhibit superior effector functions as compared to known antibodies such as infliximab (IFX).

The invention therefore relates to the subject matter defined in the following items [1] to [88]:

[1] An antibody comprising a TNFα-binding domain and an FcRn-binding site, having a high affinity to human FcRn at pH 6, said high affinity being characterized by a dissociation equilibrium constant ($K_D$) of less than 100 nM, and further having low affinity to human FcRn at pH 7.4, said low affinity being characterized by a $K_D$ of greater than 1 μM, wherein the amino acid sequence of the antibody comprises the amino acid 434W.

[2] The antibody of item [1], wherein the amino acid sequence of the antibody further comprises the amino acid 428E and/or the amino acid 311R.

[3] The antibody of item [1] or [2], wherein the amino acid sequence of the antibody comprises the amino acids 311R, 428E and 434W.

[4] The antibody of any one of the preceding items, wherein the antibody is obtained by substituting tryptophan for asparagine at position 434 (N434W), optionally substituting glutamic acid for methionine at position 428 (M428E), and optionally substituting arginine for glutamine at position 311 (Q311R).

[5] The antibody of any one of the preceding items, wherein the antibody is obtained by substituting glutamic acid for methionine at position 428 (M428E).

[6] The antibody of any one of the preceding items, wherein the antibody is obtained by substituting arginine for glutamine at position 311 (Q311R).

[7] The antibody of any one of the preceding items, comprising a heavy chain which comprises the amino acid sequence as shown in SEQ ID NO:13.
[8] The antibody of any one of the preceding items, having an affinity to human FcRn at pH 6 that is greater than that of infliximab.
[9] The antibody of any one of the preceding items, wherein said high affinity to human FcRn at pH 6 is characterized by a dissociation constant $K_D$ of less than 50 nM.
[10] The antibody of any one of the preceding items, wherein said high affinity to human FcRn at pH 6 is characterized by a dissociation constant $K_D$ of less than 25 nM.
[11] The antibody of any one of the preceding items, wherein said high affinity to human FcRn at pH 6 is characterized by a dissociation constant $K_D$ of less than 10 nM.
[12] The antibody of any one of the preceding items, having an affinity to human FcRn at pH 6 that is characterized by a dissociation constant $K_D$ in the range from 1 nM to 500 nM, or from 2 nM to 100 nM, or from 3 nM to 50 nM, or from 4 nM to 25 nM, or from 5 nM to 10 nM.
[13] The antibody of any one of the preceding items, wherein said high affinity, or said $K_D$ characterizing said high affinity, is determined by surface plasmon resonance (SPR).
[14] The antibody of any one of the preceding items, wherein said low affinity to human FcRn at pH 7.4 is characterized by a $K_D$ of greater than 10 μM.
[15] The antibody of any one of the preceding items, wherein said $K_D$ characterizing the affinity to human FcRn at pH 7.4 is determined by SPR.
[16] The antibody of any one of items [1] to [15], wherein the affinity to human FcRn at pH 7.4 is so low that a $K_D$ value cannot be determined by SPR.
[17] The antibody of any one of the preceding items, which binds to human TNFα with a $K_D$ of less than 200 pM.
[18] The antibody of any one of the preceding items, which binds to human TNFα with a $K_D$ of less than 100 pM.
[19] The antibody of any one of the preceding items, which binds to human TNFα with a $K_D$ of less than 50 pM.
[20] The antibody of any one of the preceding items, which binds to human TNFα with a $K_D$ of less than 25 pM.
[21] The antibody of any one of the preceding items, which binds to human TNFα with a $K_D$ of less than 10 pM.
[22] The antibody of any one of the preceding items, which is transported across a polarized cell monolayer from the apical side to the basolateral side.
[23] The antibody of any one of the preceding items, which is transported across a polarized cell monolayer from the apical side to the basolateral side in greater amount than a control antibody comprising a light chain having the amino acid sequence as shown in SEQ ID NO:1 and a heavy chain having the amino acid sequence as shown in SEQ ID NO:2.
[24] The antibody of any one of the preceding items, which is transported across a polarized cell monolayer from the apical side to the basolateral side in greater amount than infliximab.
[25] The antibody of item [24], wherein the amount of antibody transported across the polarized cell monolayer is greater than twice the amount of infliximab transported across the polarized cell monolayer.
[26] The antibody of any one of items [23] to [25], wherein said amount refers to the mass of antibody transported across the polarized cell monolayer within four hours.
[27] The antibody of any one of items [22] to [26], wherein the amount of antibody transported across the polarized cell monolayer is greater than two times the amount of a parent immunoglobulin transported across the polarized cell monolayer, wherein said parent immunoglobulin differs from said antibody only in that its Fc region has only wild type amino acids.
[28] The antibody of any one of the preceding items, wherein a greater percentage of the antibody than that of infliximab is transported across a polarized cell monolayer from the apical side to the basolateral side in the presence of a tenfold excess of competing immunoglobulins, wherein the percentage refers to the total mass of immunoglobulins transported across the polarized cell monolayer.
[29] The antibody of item [28], wherein the percentage of the antibody transported across the polarized cell monolayer is greater than three times the percentage of a parent immunoglobulin transported across the polarized cell monolayer, wherein said parent immunoglobulin differs from said antibody only in that its Fc region has only wild type amino acids.
[30] The antibody of item [28] or [29], wherein the percentage of the antibody transported across the polarized cell monolayer is greater than three times the percentage of infliximab transported across the polarized cell monolayer.
[31] The antibody of any one of items [22] to [30], wherein said polarized cell monolayer is a monolayer of polarized T84 cells.
[32] The antibody of any one of the preceding items, binding to CD64 with a $K_D$ of less than 100 nM, preferably less than 10 nM.
[33] The antibody of any one of the preceding items, binding to CD32a(H) with a $K_D$ of less than 10 μM.
[34] The antibody of any one of the preceding items, binding to CD32a(R) with a $K_D$ of less than 10 μM.
[35] The antibody of any one of the preceding items, binding to CD32b with a $K_D$ of less than 10 μM.
[36] The antibody of any one of the preceding items, binding to CD16a(V) with a $K_D$ of less than 500 nM, preferably less than 100 nM.
[37] The antibody of any one of the preceding items, binding to CD16a(F) with a $K_D$ of less than 10 μM, preferably less than 1 μM.
[38] The antibody of any one of the preceding items, binding to CD16b(NA2) with a $K_D$ of less than 10 μM, preferably less than 1 μM.
[39] The antibody of any one of the preceding items, binding to human C1q at a higher strength than infliximab.
[40] The antibody of any one of the preceding items, having a greater complement-dependent cytotoxicity of rabbit complement than infliximab, in terms of relative $EC_{50}$ and/or relative maximal death.
[41] The antibody of any one of the preceding items, capable of inducing CD14+CD206+ macrophages at a level equal to or greater than infliximab.

[42] The antibody of any one of the preceding items, capable of suppressing T-cell proliferation at a degree equal to or greater than infliximab.

[43] The antibody of any one of the preceding items, which is a non-fucosylated antibody or an antibody with reduced fucosylation.

[44] The antibody of any one of the preceding items, comprising (i) a $V_L$ domain comprising a CDR1 region having the amino acid sequence as shown in SEQ ID NO:3, a CDR2 region having the amino acid sequence as shown in SEQ ID NO:4, and a CDR3 region having the amino acid sequence as shown in SEQ ID NO:5, and (ii) a $V_H$ domain comprising a CDR1 region having the amino acid sequence as shown in SEQ ID NO:6, a CDR2 region having the amino acid sequence as shown in SEQ ID NO:7, and a CDR3 region having the amino acid sequence as shown in SEQ ID NO:8.

[45] The antibody of any one of the preceding items, comprising a $V_H$ domain having the amino acid sequence as shown in SEQ ID NO:9 and a $V_L$ domain having an amino acid sequence as shown in SEQ ID NO:10.

[46] The antibody of any one of the preceding items, comprising a light chain having the amino acid sequence as shown in SEQ ID NO:1 and a heavy chain having the amino acid sequence as shown in SEQ ID NO:11.

[47] The antibody of any one of items [1] to [43], wherein said antibody comprises (i) a $V_L$ domain comprising a CDR1 region having the amino acid sequence as shown in SEQ ID NO:14, a CDR2 region having the amino acid sequence as shown in SEQ ID NO:15, and a CDR3 region having the amino acid sequence as shown in SEQ ID NO:16, and (ii) a $V_H$ domain comprising a CDR1 region having the amino acid sequence as shown in SEQ ID NO:17, a CDR2 region having the amino acid sequence as shown in SEQ ID NO:18, and a CDR3 region having the amino acid sequence as shown in SEQ ID NO:19.

[48] The antibody of item [47], comprising a $V_H$ domain having the amino acid sequence as shown in SEQ ID NO:20 and a $V_L$ domain having an amino acid sequence as shown in SEQ ID NO:21 or SEQ ID NO:22.

[49] The antibody of item [47] or [48], comprising a light chain having the amino acid sequence as shown in SEQ ID NO:23 or SEQ ID NO:24 and a heavy chain having the amino acid sequence as shown in SEQ ID NO:12.

[50] The antibody of any one of the preceding items, wherein said antibody specifically binds to human TNFα.

[51] The antibody of any one of the preceding items, wherein said antibody does not significantly bind to TNFβ.

[52] The antibody of any one of the preceding items, wherein said antibody
(i) binds to human TNFα with a dissociation constant ($K_D$) of less than 125 pM;
(ii) is cross-reactive with *Macaca mulatta* TNFα and with *Macaca fascicularis* TNFα;
(iii) has a greater potency than infliximab, as determined by an L929 assay; and/or
(iv) is capable of binding to human $TNFα_{Trimer}$ in a stoichiometry (antibody: $TNFα_{Trimer}$) of at least 2.

[53] The antibody of any one of the preceding items, which binds to TNFα from *Macaca mulatta* with a $K_D$ of less than 1 nM.

[54] The antibody of any one of the preceding items, which binds to TNFα from *Macaca fascicularis* with a $K_D$ of less than 1 nM.

[55] The antibody of any one of the preceding items, wherein the potency of the antibody to inhibit TNFα-induced apoptosis relative to that of infliximab (relative potency), determined in an L929 assay, is greater than 3.5, and wherein said relative potency is the ratio of the $IC_{50}$ value in ng/mL of infliximab in the L929 assay to the $IC_{50}$ value in ng/mL of the antibody in the L929 assay.

[56] The antibody of any one of the preceding items, wherein the melting temperature of the variable domain of the antibody in scFv format, determined by differential scanning fluorimetry, is at least 65° C.

[57] The antibody of any one of the preceding items, wherein the melting temperature of the variable domain of the antibody in scFv format, determined by differential scanning fluorimetry, is at least 68° C.

[58] The antibody of any one of the preceding items, wherein the melting temperature, determined by differential scanning fluorimetry, is at least 70° C.

[59] The antibody of any one of the preceding items, wherein the antibody is capable of blocking the interaction between human TNFα and TNF receptor I (TNFRI).

[60] The antibody of any one of the preceding items, wherein the antibody is capable of blocking the interaction between human TNFα and TNF receptor II (TNFRII).

[61] The antibody of any one of the preceding items, which is capable of inhibiting cell proliferation of peripheral blood mononuclear cells in a mixed lymphocyte reaction.

[62] The antibody of any one of the preceding items, which is capable of inhibiting LPS-induced secretion of interleukin-1β from $CD14^+$ monocytes.

[63] The antibody of item [62], wherein the $IC_{50}$ value for inhibiting LPS-induced secretion of interleukin-1β is less than 1 nM.

[64] The antibody of item [63], wherein said $IC_{50}$ value for inhibiting LPS-induced secretion of interleukin-1β, on a molar basis, is lower than that of adalimumab.

[65] The antibody of any one of the preceding items, which is capable of inhibiting LPS-induced secretion of TNFα from CD14 monocytes.

[66] The antibody of item [65], wherein the $IC_{50}$ value for inhibiting LPS-induced secretion of TNFα is less than 1 nM.

[67] The antibody of item [66], wherein said $IC_{50}$ value for inhibiting LPS-induced secretion of TNFα, on a molar basis, is lower than that of adalimumab.

[68] The antibody of any one of the preceding items, which is an immunoglobulin G (IgG), preferably an IgG1.

[69] A nucleic acid encoding the antibody of any one of the preceding items.

[70] A vector or plasmid comprising the nucleic acid of item [69].

[71] A cell comprising the nucleic acid of item [69] or the vector or plasmid of item [70].

[72] A method of preparing the antibody of any one of items [1] to [68], comprising culturing the cell of item [71] in a medium under conditions that allow expression of the nucleic acid encoding the antibody, and recovering the antibody from the cells or from the medium.

[73] The antibody of any one of items [1] to [68] for use in the treatment of an inflammatory condition or a TNFα-related disorder.

[74] The antibody for use according to item [73], wherein said inflammatory disorder is selected from the list of diseases and disorders listed in Section "Disorders to be treated" below.

[75] The antibody for use according to item [73], wherein said inflammatory disorder is an inflammatory disorder of the gastrointestinal tract.

[76] The antibody for use according to item [75], wherein said inflammatory disorder of the gastrointestinal tract is inflammatory bowel disease.

[77] The antibody for use according to item [75] or [76], wherein said inflammatory disorder of the gastrointestinal tract is Crohn's disease.

[78] The antibody for use according to item [77], wherein said Crohn's disease is selected from the group consisting of ileal, colonic, ileocolonic, and/or isolated upper Crohn's disease (gastric, duodenal and/or jejunal) and including non-stricturing/non-penetrating, stricturing, penetrating and perianal disease behavior, allowing any combination of localization and disease behavior of any of the above mentioned.

[79] The antibody for use according to item [75] or [76], wherein said inflammatory disorder of the gastrointestinal tract is ulcerative colitis.

[80] The antibody for use according to item [79], wherein said ulcerative colitis is selected from the group consisting of ulcerative proctitis, proctosigmoiditis, left-sided colitis, pan-ulcerative colitis, and pouchitis.

[81] The antibody for use according to item [75] or [76], wherein said inflammatory disorder of the gastrointestinal tract is microscopic colitis.

[82] The antibody for use according to item [73], wherein said inflammatory disorder is arthritis.

[83] The antibody for use according to item [73] or [82], wherein said inflammatory disorder is rheumatoid arthritis.

[84] The antibody for use according to any one of items [73] to [83], wherein said method comprises orally administering the antibody to a subject.

[85] The antibody for use according to any one of items [73] to [84], wherein said method comprises topically applying the antibody.

[86] A pharmaceutical composition comprising the antibody of any one of items [1] to [68].

[87] A method for improving the transcytosis of an antibody directed against TNFα, comprising introducing the substitutions Q311R, M428E and N434W in the amino acid sequence of the antibody.

[88] A method for extending the plasma half-life of an antibody directed against TNFα, comprising introducing the substitutions Q311R, M428E and N434W in the amino acid sequence of the antibody.

DETAILED DESCRIPTION

Figure 1:
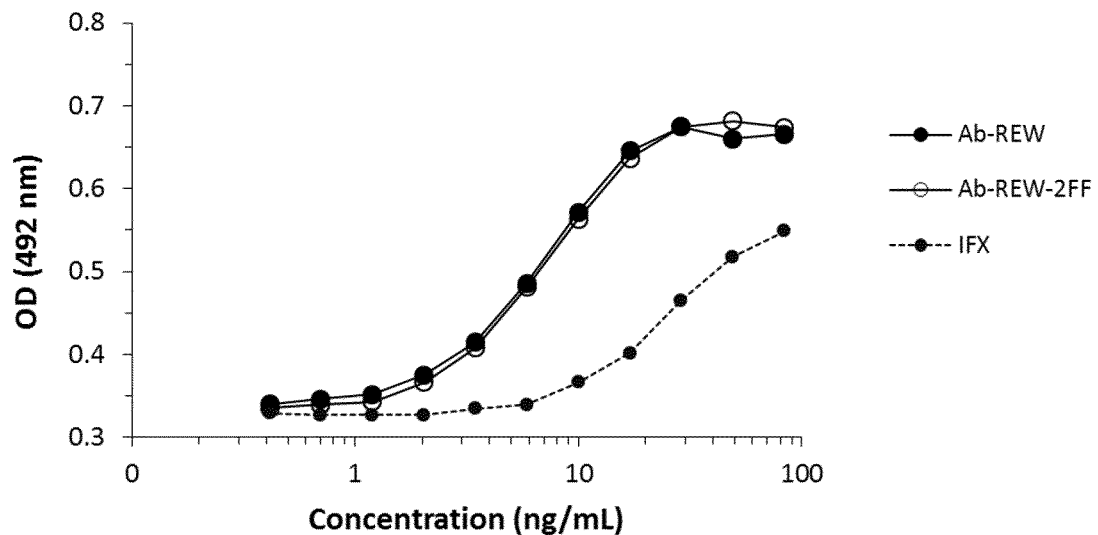
FIG. 1: Potency of anti-TNFα antibody variants to neutralize human TNFα in the L929 assay. Dose response curves for anti-TNFα antibody variants and the reference infliximab are shown.

The present invention relates to an antibody that is capable of binding to TNFα and comprises an FcRn-binding site. In accordance with this application, an antibody comprises an FcRn-binding site if it is capable of binding to FcRn, preferably to human FcRn, at pH 6. Binding to FcRn at pH 6 can be determined by SPR, e.g. as described in Example 4 of this application. If binding of an antibody to FcRn at pH 6 can be detected by SPR, such antibody has an FcRn binding site. The antibody of the invention has a high affinity to human FcRn at pH 6, characterized by a dissociation equilibrium constant ($K_D$) of less than 100 nM. The antibody further has a low affinity to human FcRn at pH 7.4, characterized by a $K_D$ of greater than 1 μM. The amino acid sequence of the antibody comprises the amino acid tryptophan at position 434 (EU numbering).

Throughout the present specification and claims, the Kabat numbering system is generally used when referring to a residue in the variable domain (approximately, residues 1-107 of the light chain and residues 1-113 of the heavy chain) (Kabat et al., *Sequences of Immunological Interest.* 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., *Sequences of Proteins of Immunological Interest,* 5th Ed. Public Health Service, National Institutes of Health, Bethesda, Md. (1991)

expressly incorporated herein by reference). Unless stated otherwise herein, references to residues numbers in the variable domain of antibodies means residue numbering by the Kabat numbering system. Unless stated otherwise herein, references to residue numbers in the constant domain of antibodies means residue numbering by the EU numbering system (see e.g., WO 2006/073941).

Antibody

In the context of the present application, the term "antibody" is used as a synonym for "immunoglobulin" (Ig), which is defined as a protein belonging to the class IgG, IgM, IgE, IgA, or IgD (or any subclass thereof), and includes all conventionally known antibodies and functional fragments thereof. In the context of the present invention, a "functional fragment" of an antibody/immunoglobulin is defined as antigen-binding fragment or other derivative of a parental antibody that essentially maintains one or more of the properties of such parental antibody. An "antigen-binding fragment" or "antigen-binding domain" of an antibody/immunoglobulin is defined as fragment (e.g., a variable region of an IgG) that retains the antigen-binding region. An "antigen-binding region" of an antibody typically is found in one or more hypervariable region(s) of an antibody, i.e., the CDR-1, -2, and/or -3 regions. The antibodies of the present invention may be part of bi- or multifunctional constructs.

Preferably the antibody is a monoclonal antibody. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Monoclonal antibodies can be prepared using a wide variety of techniques known in the art including the use of hybridoma, recombinant, and phage display technologies, or a combination thereof. (Harlow and Lane, "Antibodies, A Laboratory Manual" CSH Press 1988, Cold Spring Harbor N.Y.).

In other embodiments, including embodiments relating to the in vivo use of the anti-TNFα antibodies in humans, chimeric, primatized, humanized, or human antibodies can be used. In a preferred embodiment, the antibody is a human antibody or a humanized antibody, more preferably a monoclonal human antibody or a monoclonal humanized antibody.

In another particular embodiment the antibody of the invention is an immunoglobulin, preferably an immunoglobulin G (IgG). The subclass of the IgG of the invention is not limited and includes $IgG_1$, $IgG_2$, $IgG_3$, and $IgG_4$. Preferably, the IgG of the invention is of subclass 1, 2 or 4, i.e. it is an $IgG_1$, $IgG_2$, or $IgG_4$ molecule, respectively. Most preferably, the IgG of the invention is of subclass 1, i.e. it is an $IgG_1$ molecule.

TNFα-Binding Domain

The TNFα-binding domain of the antibody of the invention is not particularly limited. It can be derived from any antibody that is capable of binding to TNFα.

Preferably, the antibody of the invention specifically binds to TNFα. As used herein, an antibody "specifically recognizes", or "specifically binds to" human TNFα, when the antibody is able to discriminate between human TNFα and one or more reference molecule(s). Preferably, the $IC_{50}$ value for binding to each of the reference molecules is at least 1,000 times greater than the $IC_{50}$ value for binding to TNFα. In its most general form (and when no defined reference is mentioned), "specific binding" is referring to the ability of the antibody to discriminate between human TNFα and an unrelated biomolecule, as determined, for example, in accordance with a specificity assay methods known in the art. Such methods comprise, but are not limited to, Western blots and ELISA tests. For example, a standard ELISA assay can be carried out. Typically, determination of binding specificity is performed by using not a single reference biomolecule, but a set of about three to five unrelated biomolecules, such as milk powder, BSA, transferrin or the like. In one embodiment, specific binding refers to the ability of the antibody to discriminate between human TNFα and human TNFβ.

The antibody of the invention comprises a $V_L$ domain and a $V_H$ domain. The $V_L$ domain comprises a CDR1 region (CDRL1), a CDR2 region (CDRL2), a CDR3 region (CDRL3) and Framework regions. The $V_H$ domain comprises a CDR1 region (CDRH1), a CDR2 region (CDRH2), a CDR3 region (CDRH3) and Framework regions.

The term "CDR" refers to one of the six hypervariable regions within the variable domains of an antibody that mainly contribute to antigen binding. One of the most commonly used definitions for the six CDRs was provided by Kabat E. A. et al., (1991) Sequences of proteins of immunological interest. NIH Publication 91-3242). As used herein, Kabat's definition of CDRs only apply for CDR1, CDR2 and CDR3 of the light chain variable domain (CDR L1, CDR L2, CDR L3, or L1, L2, L3), as well as for CDR2 and CDR3 of the heavy chain variable domain (CDR H2, CDR H3, or H2, H3). CDR1 of the heavy chain variable domain (CDR H1 or H1), however, as used herein is defined by the following residues (Kabat numbering): It starts with position 26 and ends prior to position 36.

In one embodiment of the present invention, the antibody of the invention is an anti-TNFα antibody as disclosed in any one of PCT applications PCT/EP2017/056218, PCT/EP2017/056246, PCT/EP2017/056237 and PCT/EP2017/056227 as originally filed. In yet another embodiment of the present invention, the antibody is an anti-TNFα antibody with a light chain variable domain and/or a heavy chain variable domain comprising complementarity-determining regions (CDRs) with amino acid sequences as disclosed in PCT applications PCT/EP2017/056218, PCT/EP2017/056246, PCT/EP2017/056237 and PCT/EP2017/056227 as originally filed.

In a preferred embodiment of the present invention, the antibody is an anti-TNFα antibody with a light chain variable domain and/or a heavy chain variable domain comprising one or more CDRs with amino acid sequences as disclosed in PCT/EP2017/056218, PCT/EP2017/056246, PCT/EP2017/056237, or PCT/EP2017/056227. In another preferred embodiment of the present invention, the antibody is an anti-TNFα antibody with a light chain variable domain and a heavy chain variable domain comprising CDRs with amino acid sequences as disclosed in claim 2 of PCT/EP2017/056218, in claim 2 of PCT/EP2017/056246, in claim 2 of PCT/EP2017/056237 or in claim 2 PCT/EP2017/056227, as originally filed. In yet another preferred embodiment of the present invention, the anti-TNFα antibody is selected from the group consisting of anti-TNFα antibodies comprising a heavy chain variable domain amino acid sequence and/or a light chain variable domain amino acid sequence according to claim 4 of PCT/EP2017/056218, claims 5 and 6 of PCT/EP2017/056246, claims 5 and 6 of PCT/EP2017/056237, claim 4 of PCT/EP2017/056227, and combinations thereof. The disclosure of each of the international patent applications PCT/EP2017/056218, PCT/EP2017/056246, PCT/EP2017/056237 and PCT/EP2017/056227 is incorporated herein in its entirety. They form part of the disclosure of the present application.

In a particular embodiment, the antibody of the invention comprises (i) a $V_L$ domain comprising a CDR1 region having the amino acid sequence as shown in SEQ ID NO:3, a CDR2 region having the amino acid sequence as shown in SEQ ID NO:4, and a CDR3 region having the amino acid sequence as shown in SEQ ID NO:5, and (ii) a $V_H$ domain comprising a CDR1 region having the amino acid sequence as shown in SEQ ID NO:6, a CDR2 region having the amino acid sequence as shown in SEQ ID NO:7, and a CDR3 region having the amino acid sequence as shown in SEQ ID NO:8.

In a more preferred embodiment, the antibody of the invention of the invention comprises a $V_H$ domain having the amino acid sequence as shown in SEQ ID NO:9. In another more preferred embodiment the antibody comprises a $V_L$ domain having the amino acid sequence as shown in SEQ ID NO:10. Most preferably, the antibody of the invention comprises (i) a $V_H$ domain having the amino acid sequence as shown in SEQ ID NO:9, and (ii) a $V_L$ domain having the amino acid sequence as shown in SEQ ID NO:10.

In another particular embodiment, the antibody of the invention comprises (i) a $V_L$ domain comprising a CDR1 region having the amino acid sequence as shown in SEQ ID NO:14, a CDR2 region having the amino acid sequence as shown in SEQ ID NO:15, and a CDR3 region having the amino acid sequence as shown in SEQ ID NO:16, and (ii) a $V_H$ domain comprising a CDR1 region having the amino acid sequence as shown in SEQ ID NO:17, a CDR2 region having the amino acid sequence as shown in SEQ ID NO:18, and a CDR3 region having the amino acid sequence as shown in SEQ ID NO:19.

In a more preferred embodiment, the antibody of the invention comprises a $V_H$ domain having the amino acid sequence as shown in SEQ ID NO:20. In another more preferred embodiment the antibody comprises a $V_L$ domain having the amino acid sequence as shown in SEQ ID NO:21 or SEQ ID NO:22. Most preferably, the antibody of the invention comprises (i) a $V_H$ domain having the amino acid sequence as shown in SEQ ID NO:20, and (ii) a $V_L$ domain having the amino acid sequence as shown in SEQ ID NO:21 or SEQ ID NO:22.

The antibody of the invention has a high affinity to human TNFα. The term "$K_D$," refers to the dissociation equilibrium constant of a particular antibody-antigen interaction. Typically, the antibody of the invention binds to human TNFα with a dissociation equilibrium constant ($K_D$) of less than approximately $2\times10^{-10}$ M, preferably less than $1.5\times10^{-10}$ M, preferably less than $1.25\times10^{-10}$ M, more preferably less than $1\times10^{-10}$ M, most preferably less than $7.5\times10^{-11}$ M or even less than $5\times10^{-11}$ M, as determined using surface plasmon resonance (SPR) technology in a BIACORE instrument. In particular, the determination of the $K_D$ is carried out as described in Example 1.

Modifications Affecting Affinity to FcRn

The antibody of the invention comprises an amino acid sequence which differs from that of a native sequence of a wild-type antibody by virtue of at least one "amino acid modification" as herein defined. The at least one amino acid modification affects the affinity of the antibody to human FcRn. Typically, the at least one amino acid modification increases the affinity of the antibody to human FcRn at pH 6. In one embodiment, the at least one amino acid modification increases the affinity of the antibody to human FcRn at pH 6, wherein it does not substantially change the affinity to human FcRn at pH 7.4. Preferably, the modified antibody has at least one amino acid substitution compared to the amino acid sequence of a wild-type antibody or of a parent antibody, e.g. from about one to about ten amino acid substitutions, and preferably from about one to about five amino acid substitutions. Preferably, the at least one amino acid modification is within the FcRn binding site of the antibody. The antibody may have one or more amino acid modifications outside the FcRn binding site of the antibody which affect FcRn binding, e.g. by structural changes. The amino acid modification(s) can be generated by methods that are known per se, e.g. by site-directed mutagenesis as described in "Antibody Engineering—Methods and Protocols", edited by Patrick Chames, $2^{nd}$ ed., 2012, Chapter 31 (ISBN 978-1-61779-973-0).

The antibody of the invention comprises the amino acid tryptophan at position 434 (EU numbering). This is referred to as "434W" herein. The native amino acid at position 434 of non-modified human IgG antibodies is asparagine (N). Thus, the antibody of the invention can be obtained by introducing the mutation N434W into an antibody. Preferably, the antibody of the invention is obtainable or obtained by substituting tryptophan for asparagine at position 434.

The antibody of the invention comprises the amino acid glutamic acid at position 428 (EU numbering). This is referred to as "428E" herein. The native amino acid at position 428 of non-modified human IgG antibodies is methionine (M). Thus, the antibody of the invention can be obtained by introducing the mutation M428E into an antibody. Preferably, the antibody of the invention is obtainable or obtained by substituting glutamic acid for methionine at position 428.

Preferably, the antibody of the present invention further comprises the amino acid arginine at position 311 (EU numbering). This is referred to as "311R" herein. The native amino acid at position 311 of non-modified human IgG antibodies is glutamine (Q). Thus, the antibody of the invention can be obtained by introducing the mutation Q311R into an antibody. Preferably, the antibody of the invention is obtainable or obtained by substituting glutamine for arginine at position 311.

In one embodiment, the antibody of the invention comprises the amino acid 434W and the amino acid 428E. In another embodiment, the antibody of the invention comprises the amino acid 434W and the amino acid 311R. In a preferred embodiment of the invention, the antibody comprises the amino acids 434W, 428E and 311R. This antibody is obtainable by introducing the mutations Q311R, M428E and N434W into an antibody.

The remaining amino acid sequence of the constant domain may be identical to the native amino acid sequence of a typical human IgG. It is possible, however, that the amino acid sequence of the antibody comprises one or more additional mutations or substitutions to the native amino acid sequence of the Fc region of a native antibody, as long as the antibody still has TNFα-binding activity and effector functions.

In a preferred embodiment, the Fc region of the antibody of the invention, including the hinge region, comprises or consists of the amino acid sequence as shown in SEQ ID NO:13.

In one embodiment, the heavy chain of the antibody of the invention has the amino acid sequence as shown in SEQ ID NO:11. Preferably, this antibody further comprises a light chain having the amino acid sequence as shown in SEQ ID NO:1.

In another embodiment, the heavy chain of the antibody of the invention has the amino acid sequence as shown in SEQ ID NO:12. Preferably, this antibody further comprises a light chain having the amino acid sequence as shown in SEQ ID NO:23 or SEQ ID NO:24.

In a preferred aspect of the invention, the antibody of the invention is a non-fucosylated antibody or an antibody having reduced fucosylation.

The term "antibody having reduced fucosylation", as used herein, refers to an antibody in which less than 90% of the N-glycans of the antibody are fucosylated. Methods to determine the percentage of fucosylation are known in the art. Preferably, the percentage of fucosylation is determined as described in Example 11 of this application.

In one embodiment, less than 75%, or less than 50%, or less than 25% of the N-glycans of the antibody are fucosylated. Most preferably, less than 15% of the N-glycans of the antibody are fucosylated. In a particular embodiment, the N-glycans of the antibody of the invention do not contain any fucose.

Preferably, less than 90% of the N-glycans at N297 (EU numbering) of the antibody are fucosylated. In another embodiment, less than 75%, or less than 50%, or less than 25% of the N-glycans at N297 (EU numbering) of the antibody are fucosylated. Most preferably, less than 15% of the N-glycans at N297 (EU numbering) of the antibody are fucosylated.

In another embodiment, the N-glycans at N297 of the antibody do not contain any fucose.

Non-fucosylated antibodies, sometimes also referred to as afucosylated antibodies, can be generated by various methods. For example, the synergistic knockdown of the genes for α1,6-fucosyltransferase (FUT8) and GDP-mannose 4,6-dehydratase (GMD) in CHO cells can be used to produce monoclonal antibody variants that are fully afucosylated and ADCC-enhanced (see, e.g., Imai-Nishiya et al. (2007) BMC Biotechnol. 7, 84). A method using zinc-finger nucleases (ZFNs) cleaving the FUT8 gene in a region encoding the catalytic core of the α1,6-fucosyltransferase and thus disrupting the corresponding enzymatic function in CHO cells can be used to produce monoclonal antibodies completely lacking core fucose (see, e.g., Malphettes et al. (2010) Biotechnol. Bioeng. 106, 774-783).

Antibodies having reduced fucosylation can be prepared by addition of a decoy substrate such as 2-deoxy-2-fluoro-2-fucose to the culture medium (see, e.g., Dekker et al. (2016) Sci Rep 6:36964), resulting in a reduced incorporation of fucose in the IgG-Fc glycans.

In another embodiment, the antibody of the invention has a high sialic acid content. In increase in sialylation can be achieved, e.g. by simultaneous transfection of cytidine monophosphate-sialic acid synthase (CMP-SAS), cytidine monophosphate-sialic acid transporter (CMP-SAT), and a 2,3-sialyltransferases (see, e.g., Son et al. (2011) Glycobiology 21, 1019-1028).

Affinity to FcRn

The affinity at pH 6 to human FcRn of the antibody of the invention is high. The high affinity binding of the antibody to human FcRn at pH 6 is characterized by a $K_D$ value of less than 100 nM. Preferably, the $K_D$ value of the high affinity binding at pH 6 is less than 75 nM, or less than 50 nM, or less than 25 nM, or even less than 10 nM. For example, the $K_D$ value characterizing the affinity to human FcRn at pH 6 may be in the range from 1 nM to 500 nM, or from 2 nM to 100 nM, or from 3 nM to 50 nM, or from 4 nM to 25 nM, or from 5 nM to 10 nM.

In a preferred embodiment, the affinity of the antibody of the invention to human FcRn at pH 6 is greater than the affinity of infliximab to human FcRn at pH 6.0.

The affinity of the antibody of the invention to human FcRn is preferably determined by surface plasma resonance (SPR), for example as described in Example 4 of this application.

The antibody of the present invention typically has a low affinity to human FcRn at pH 7.4. The low affinity is characterized by a $K_D$ value of greater than 1 μM. Preferably, the low affinity to human FcRn at pH 7.4 is characterized by a $K_D$ value of greater than 2 μM, or greater than 5 μM, or greater than 10 μM.

In a particular embodiment, the low affinity is so low that a $K_D$ value cannot be determined by SPR.

In a special embodiment, the ratio of (i) a $K_D$ value for binding of the antibody of the invention to human FcRn at pH 7.4 to (ii) a $K_D$ value for binding to human FcRn at pH 6.0, is at least 100. Preferably, this ratio is at least 200, or at least 300, or at least 400, or at least 500, or at least 600, or at least 700, or at least 800, or at least 900, or at least 1000.

Functional Properties of the Antibody

The antibody of the invention is efficiently transported across a polarized cell monolayer from the apical side to the basolateral side. Typically, the transport across the polarized cell monolayer is in a greater amount than that of infliximab, wherein the amount of antibody in infliximab refers to the mass/cm² of the polarized cell monolayer. The amount of antibody transported across the polarized cell monolayer, relative to the amount of infliximab transported across the polarized cell monolayer, is at least 110%, preferably at least 125%, more preferably at least 150%, or at least 175%, or at least 200% (wherein the amount of transported infliximab is set to 100%).

Furthermore, the antibody is specifically transported across the polarized cell monolayer from the apical side to the basolateral side in the presence of an excess of competing immunoglobulins. This is referred to as specific transport herein.

The percentage of the total mass of immunoglobulins transported across the polarized cell monolayer is greater than the percentage of infliximab transported across the polarized cell monolayer from the apical side to the basolateral side in the presence of a 10-fold excess of competing immunoglobulins. The percentage of antibody of the invention transported across the polarized cell monolayer in the presence of a 10-fold excess of unrelated immunoglobulins, relative to the percentage of infliximab transported across the polarized cell monolayer in the presence of a 10-fold excess of unrelated antibodies, is at least 150%, or at least 200%, or at least 250%, or at least 300% (infliximab is set to be 100%).

Preferably, the polarized cell monolayer is a monolayer of polarized T84 cells. The transport assay mimicking process of transcytosis can be carried out as described in Example 5 of this application.

The antibody of the invention binds to CD64, CD32a(H), CD32a(R), CD32b, CD16a(V), CD16a(F) and CD16b (NA2).

The antibody of the invention typically binds to CD64 with a $K_D$ of less than 100 nM, preferably less than 10 nM.

The antibody of the invention typically binds to CD32a (H) with a $K_D$ of less than 10 μM.

The antibody of the invention typically binds to CD32a (R) with a $K_D$ of less than 10 μM.

The antibody of the invention typically binds to CD32b with a $K_D$ of less than 10 μM.

The antibody of the invention typically binds to CD16a (V), e.g. with a $K_D$ of less than 500 nM, preferably less than 100 nM.

The antibody of the invention typically binds to CD16a (F), e.g. with a $K_D$ of less than 10 μM, preferably less than 1 μM.

The antibody of the invention typically binds to CD16b (NA2), e.g. with a $K_D$ of less than 10 μM, preferably less than 1 μM.

The antibody of the invention further binds to human C1q. Preferably, this binding is stronger than the binding of infliximab to human C1q.

The antibody of the invention further has complement-dependent cytotoxicity (CDC) of rabbit complement. This CDC of the antibody of the invention is preferably greater than that of infliximab, in terms of relative $EC_{50}$ and/or relative maximal death.

The antibody of the invention is further capable of inducing CD14+CD206 macrophages. The level of induction is preferably comparable to, equal to, or greater than that of infliximab.

The antibody of the invention is further capable of suppressing T-cell proliferation. The degree of suppression of T-cell proliferation is preferably comparable to, equal to, or greater than that of infliximab.

Pharmaceutical Compositions and Treatment

Treatment of a disease encompasses the treatment of patients already diagnosed as having any form of the disease at any clinical stage or manifestation; the delay of the onset or evolution or aggravation or deterioration of the symptoms or signs of the disease; and/or preventing and/or reducing the severity of the disease.

A "subject" or "patient" to whom an anti-TNFα antibody is administered can be a mammal, such as a non-primate (e.g., cow, pig, horse, cat, dog, rat, etc.) or a primate (e.g., monkey or human). In certain aspects, the human is a pediatric patient. In other aspects, the human is an adult patient.

Compositions comprising an anti-TNFα antibody and, optionally one or more additional therapeutic agents, such as the second therapeutic agents described below, are described herein. The compositions typically are supplied as part of a sterile, pharmaceutical composition that includes a pharmaceutically acceptable carrier. This composition can be in any suitable form (depending upon the desired method of administering it to a patient).

The anti-TNFα antibodies can be administered to a patient by a variety of routes such as orally, transdermally, subcutaneously, intranasally, intravenously, intramuscularly, intrathecally, topically or locally, e.g. mucosally. The most suitable route for administration in any given case will depend on the particular antibody, the subject, and the nature and severity of the disease and the physical condition of the subject. Typically, an anti-TNFα antibody will be administered intravenously.

In a particularly preferred embodiment, the antibody of the invention is administered orally. If the administration is via the oral route the antibody is preferably an IgG, most preferably an IgG1.

In typical embodiments, an anti-TNFα antibody is present in a pharmaceutical composition at a concentration sufficient to permit intravenous administration at 0.5 mg/kg body weight to 20 mg/kg body weight. In some embodiments, the concentration of antibody suitable for use in the compositions and methods described herein includes, but is not limited to, 0.5 mg/kg, 0.75 mg/kg, 1 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, or a concentration ranging between any of the foregoing values, e.g., 1 mg/kg to 10 mg/kg, 5 mg/kg to 15 mg/kg, or 10 mg/kg to 18 mg/kg.

The effective dose of an anti-TNFα antibody can range from about 0.001 to about 750 mg/kg per single (e.g., bolus) administration, multiple administrations or continuous administration, or to achieve a serum concentration of 0.01-5000 μg/ml per single (e.g., bolus) administration, multiple administrations or continuous administration, or any effective range or value therein depending on the condition being treated, the route of administration and the age, weight and condition of the subject. In case of oral administration, the serum concentration may be very low or even below the detection limit. In certain embodiments, each dose can range from about 0.5 mg to about 50 mg per kilogram of body weight or from about 3 mg to about 30 mg per kilogram body weight. The antibody can be formulated as an aqueous solution.

In a particularly preferred embodiment, the antibody of the invention is administered orally. If the administration is via the oral route the antibody is preferably an IgG, most preferably an $IgG_1$. If the antibody is administered orally, the daily dose of antibody is typically in the range of about 0.01 mg/kg to about 100 mg/kg of body weight, or about 0.05 mg/kg to about 50 mg/kg of body weight, or about 0.1 mg/kg to about 25 mg/kg of body weight, or about 0.15 mg/kg to about 10 mg/kg of body weight, or about 0.16 mg/kg to about 5 mg/kg of body weight, or about 0.2 mg/kg to about 2 mg/kg of body weight, or about 0.2 mg/kg to about 1 mg/kg of body weight, Generally, advantageous doses are doses of 1 to 200 mg per day, preferably 5 to 100 or 10 to 50 mg per day.

Pharmaceutical compositions can be conveniently presented in unit dose forms containing a predetermined amount of an anti-TNFα antibody per dose. Such a unit can contain 0.5 mg to 5 g, for example, but without limitation, 1 mg, 10 mg, 20 mg, 30 mg, 40 mg, 50 mg, 100 mg, 200 mg, 300 mg, 400 mg, 500 mg, 750 mg, 1000 mg, or any range between any two of the foregoing values, for example 10 mg to 1000 mg, 20 mg to 50 mg, or 30 mg to 300 mg. Pharmaceutically acceptable carriers can take a wide variety of forms depending, e.g., on the condition to be treated or route of administration.

Determination of the effective dosage, total number of doses, and length of treatment an anti-TNFα antibody thereof is well within the capabilities of those skilled in the art, and can be determined using a standard dose escalation study.

Therapeutic formulations of the anti-TNFα antibodies suitable in the methods described herein can be prepared for storage as lyophilized formulations or aqueous solutions by mixing the antibody having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives must be nontoxic to the recipients at the dosages and concentrations employed.

Buffering agents help to maintain the pH in the range which approximates physiological conditions. They can present at concentration ranging from about 2 mM to about 50 mM. Suitable buffering agents include both organic and inorganic acids and salts thereof such as citrate buffers (e.g., monosodium citrate-disodium citrate mixture, citric acid-trisodium citrate mixture, citric acid-monosodium citrate mixture, etc.), citrate-phosphate buffers, succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

The pharmaceutical composition of the invention may further comprise at least one salt, e.g. sodium chloride. The salt concentration preferably ranges from 100 mM to 200 mM, e.g. about 150 mM.

Preservatives can be added to retard microbial growth, and can be added in amounts ranging from 0.2%-1% (w/v). Suitable preservatives include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonifiers sometimes known as "stabilizers" can be added to ensure isotonicity of liquid compositions and include polyhydric sugar alcohols, preferably trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinositol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. Stabilizers can be present in the range from 0.1 to 10,000 weights per part of weight active protein.

Non-ionic surfactants or detergents (also known as "wetting agents") can be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic polyols, polyoxyethylene sorbitan monoethers (TWEEN®-20, TWEEN®-80, etc.). Non-ionic surfactants can be present in a range of about 0.05 mg/ml to about 1.0 mg/ml, or in a range of about 0.07 mg/ml to about 0.2 mg/ml.

Additional miscellaneous excipients include bulking agents (e.g., starch), chelating agents (e.g., EDTA), antioxidants (e.g., ascorbic acid, methionine, vitamin E), protease inhibitors and co-solvents.

The formulation herein can also contain a second therapeutic agent in addition to an anti-TNFα antibody thereof. Examples of suitable second therapeutic agents are provided below.

The dosing schedule can vary from once a month to daily depending on a number of clinical factors, including the type of disease, severity of disease, and the patient's sensitivity to the anti-TNFα antibody. In specific embodiments, an anti-TNFα antibody thereof is administered daily, twice weekly, three times a week, every other day, every 5 days, once weekly, every 10 days, every two weeks, every three weeks, every four weeks or once a month, or in any range between any two of the foregoing values, for example from every four days to every month, from every 10 days to every two weeks, or from two to three times a week, etc.

The dosage of an anti-TNFα antibody to be administered will vary according to the particular antibody, the subject, and the nature and severity of the disease, the physical condition of the subject, the therapeutic regimen (e.g., whether a second therapeutic agent is used), and the selected route of administration; the appropriate dosage can be readily determined by a person skilled in the art.

It will be recognized by one of skill in the art that the optimal quantity and spacing of individual dosages of an anti-TNFα antibody thereof will be determined by the nature and extent of the condition being treated, the form, route and site of administration, and the age and condition of the particular subject being treated, and that a physician will ultimately determine appropriate dosages to be used. This dosage can be repeated as often as appropriate. If side effects develop the amount and/or frequency of the dosage can be altered or reduced, in accordance with normal clinical practice.

Disorders to be Treated

The invention relates to a method of treating or preventing a human TNFα-related disease in a subject, comprising administering to the subject the antibody as defined herein. The term "TNFα-related disorder" or "TNFα-related disease" refers to any disorder, the onset, progression or the persistence of the symptoms or disease states of which requires the participation of TNFα. Exemplary TNFα-related disorders include, but are not limited to, chronic and/or autoimmune states of inflammation in general, immune mediated inflammatory disorders in general, inflammatory CNS disease, inflammatory diseases affecting the eye, joint, skin, mucous membranes, central nervous system, gastrointestinal tract, urinary tract or lung, states of uveitis in general, retinitis, HLA-B27+ uveitis, Behçet's disease, dry eye syndrome, glaucoma, Sjögren syndrome, diabetes mellitus (incl. diabetic neuropathy), insulin resistance, states of arthritis in general, rheumatoid arthritis, osteoarthritis, reactive arthritis and Reiter's syndrome, juvenile arthritis, ankylosing spondylitis, multiple sclerosis, Guillain-Barré syndrome, myasthenia gravis, amyotrophic lateral sclerosis, sarcoidosis, glomerulonephritis, chronic kidney disease, cystitis, psoriasis (incl. psoriatic arthritis), hidradenitis suppurativa, panniculitis, pyoderma gangrenosum, SAPHO syndrome (synovitis, acne, pustulosis, hyperostosis and osteitis), acne, Sweet's sydrome, pemphigus, Crohn's disease (incl. extraintestinal manifestastations), ulcerative colitis, asthma bronchiale, hypersensitivity pneumonitis, general allergies, allergic rhinitis, allergic sinusitis, chronic obstructive pulmonary disease (COPD), lung fibrosis, Wegener's granulomatosis, Kawasaki syndrome, Giant cell arteritis, Churg-Strauss vasculitis, polyarteritis nodosa, burns, graft versus host disease, host versus graft reactions, rejection episodes following organ or bone marrow transplantation, systemic and local states of vasculitis in general, systemic and cutaneous lupus erythematodes, polymyositis and dermatomyositis, sclerodermia, pre-eclampsia, acute and chronic pancreatitis, viral hepatitis, alcoholic hepatitis, postsurgical inflammation such as after eye surgery (e.g. cataract (eye lens replacement) or glaucoma surgery), joint surgery (incl. arthroscopic surgery), surgery at joint-related structures (e.g. ligaments), oral and/or dental surgery, minimally invasive cardiovascular procedures (e.g. PTCA, atherectomy, stent placement), laparoscopic and/or endoscopic intra-abdominal and gynecological procedures, endoscopic urological procedures (e.g. prostate surgery, ureteroscopy, cystoscopy, interstitial cystitis), or perioperative inflammation (prevention) in general, bullous dermatitis, neutrophilic dermatitis, toxic epidermal necrolysis, pustular dermatitis, cerebral malaria, hemolytic uremic syndrome, allograft rejection, otitis media, snakebite, erythema nodosum, myelodysplastic syndromes, primary sclerosing cholangitis, seronegative spondylartheropathy, autoimmune hematolytic anemia, orofacial granulamatosis, pyostomatitis vegetans, aphthous stomatitis, geographic tongue, migratory stomatitis, Alzheimer disease, Parkinson's disease, Hunginton's disease, Bell's palsy, Creutzfeld-Jakob disease and neuro-degenerative conditions in general.

Cancer-related osteolysis, cancer-related inflammation, cancer-related pain, cancer-related cachexia, bone metastases, acute and chronic forms of pain, irrespective whether these are caused by central or peripheral effects of TNFα and whether they are classified as inflammatory, nociceptive or neuropathic forms of pain, sciatica, low back pain, carpal tunnel syndrome, complex regional pain syndrome (CRPS), gout, postherpetic neuralgia, fibromyalgia, local pain states, chronic pain syndroms due to metastatic tumor, dismenorrhea.

Particular disorders to be treated include states of arthritis in general, rheumatoid arthritis, osteoarthritis, reactive arthritis, juvenile arthritis; psoriasis incl. psoriatic arthritis; inflammatory bowel disease, including Crohn's disease, ulcerative colitis incl. proctitis, sigmoiditis, proctosigmoiditis, left-sided colitis, extensive colitis and pancolitis, undetermined colitis, microscopic colitis incl. collagenous and lymphocytic colitis, colitis in connective tissue disease, diversion colitis, colitis in diverticular disease, eosinophilic colitis and pouchitis.

Most preferably, the antibody of the invention is used to treat an inflammatory bowel disease, in particular Crohn's disease, ulcerative colitis or microscopic colitis. The Crohn's disease may be ileal, colonic, ileocolonic or isolated upper Crohn's disease (gastric, duodenal and/or jejunal) including non-stricturing/non-penetrating, stricturing, penetrating and perianal disease behavior, allowing any combination of localization and disease behavior of any of the above mentioned. The ulcerative colitis may be ulcerative proctitis, proctosigmoiditis, left-sided colitis, pan-ulcerative colitis and pouchitis.

Combination Therapy and Other Aspects

Preferably, the patient being treated with an anti-TNFα antibody thereof is also treated with another conventional medicament. For example, a patient suffering from inflammatory bowel disease, especially if having moderate to severe disease is typically also being treated with mesalazine or derivatives or prodrugs thereof, corticosteroids, e.g. budesonide or prednisolone (oral or i.v.), immunosuppressants, e.g. azathioprine/6-mercaptopurine (6-MP) or methotrexate, cyclosporine or tacrolimus. Other medicaments which can be co-administered to the patient include other anti-TNFα antibodies (e.g. infliximab, adalimumab, etanercept, certolizumab pegol, golimumab), integrin antagonists (e.g. natalizumab, vedolizumab), anti-IL-23 antibodies (e.g. MEDI2070), anti-β7 antibodies (e.g. etrolizumab), JAK inhibitors in the JAK/STAT pathway (e.g. tofacitinib), and others. Further medicaments which can be co-administered to the patient include immunosupressants (e.g. azathioprine/6-MP or methotrexate or oral cyclosporine) in order to maintain stable and longer remission.

Yet another aspect of the invention is the use of an anti-TNFα antibody as defined hereinabove for reducing inflammation.

Yet another aspect of the invention is an anti-TNFα antibody as defined hereinabove for use in reducing inflammation in a patient suffering from an inflammatory condition.

A further aspect of this invention is a method of treating an inflammatory condition, comprising administering to a patient in need thereof an effective amount of an anti-TNFα antibody as defined hereinabove. The inflammatory condition is preferably one of the conditions described above.

A further aspect of this invention is a method of preventing an inflammatory condition, comprising administering to a patient in need thereof an effective amount of an anti-TNFα antibody as defined hereinabove. The inflammatory condition is preferably one of the conditions described above.

Yet another aspect of the present invention is a method for improving the transcytosis of an antibody directed against TNFα, comprising introducing the substitutions Q311R, M428E and N434W in the amino acid sequence of the antibody so as to obtain a modified antibody having improved transcytosis. The modified antibody is preferably an antibody as described hereinabove.

Yet another aspect of the present invention is a method for extending the plasma half-life of an antibody directed against TNFα, comprising introducing the substitutions Q311R, M428E and N434W in the amino acid sequence of the antibody so as to obtain a modified antibody having an extended plasma half-life. The modified antibody is preferably an antibody as described hereinabove. The plasma half-life may be increased by at least 10%, or least 20%, or least 30%, or least 40%, or least 50%, relative to the plasma half-life of the non-modified antibody (i.e., the parent antibody lacking the substitutions Q311R, M428E and N434W).

TABLE 1

Overview of the sequences of the sequence listing.

| SEQ ID NO: | Description of the amino acid sequence |
|---|---|
| 1 | Light chain of Ab-wt, the parent antibody of the modified antibodies used in the examples |
| 2 | Heavy chain of Ab-wt, the parent antibody of the modified antibodies used in the examples |
| 3 | CDR L1 of clone 16-22-H05 |
| 4 | CDR L2 of clone 16-22-H05 |
| 5 | CDR L3 of clone 16-22-H05 |
| 6 | CDR H1 of clone 16-22-H05 |
| 7 | CDR H2 of clone 16-22-H05 |
| 8 | CDR H3 of clone 16-22-H05 |

TABLE 1-continued

Overview of the sequences of the sequence listing.

| SEQ ID NO: | Description of the amino acid sequence |
|---|---|
| 9 | $V_H$ of humanized IgG of clone 16-22-H05 |
| 10 | $V_L$ of humanized IgG of clone 16-22-H05 |
| 11 | Heavy chain of Ab-REW (based on clone 16-22-H05) |
| 12 | Heavy chain of Ab-REW (based on clone 17-22-B03) |
| 13 | Fc region of Ab-REW (including hinge region) |
| 14 | CDR L1 of clone 17-22-B03 |
| 15 | CDR L2 of clone 17-22-B03 |
| 16 | CDR L3 of clone 17-22-B03 |
| 17 | CDR H1 of clone 17-22-B03 |
| 18 | CDR H2 of clone 17-22-B03 |
| 19 | CDR H3 of clone 17-22-B03 |
| 20 | $V_H$ of humanized IgG of clone 17-22-B03 |
| 21 | $V_L$ of humanized IgG of clone 17-22-B03 (sc08) |
| 22 | $V_L$ of humanized IgG of clone 17-22-B03 (sc02) |
| 23 | Light chain of humanized IgG of clone 17-22-B03 (sc08) |
| 24 | Light chain of humanized IgG of clone 17-22-B03 (sc02) |

EXAMPLES

Antibody Variants

Figure 9:
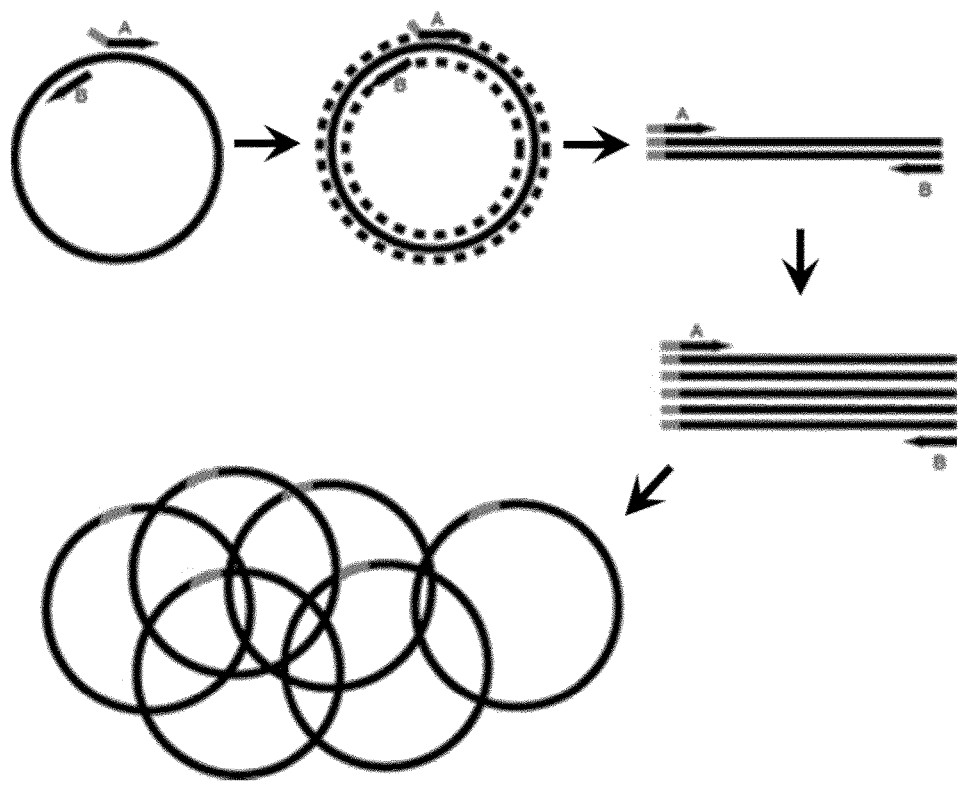
FIG. 9: Schematic presentation of site directed mutagenesis.

Several variants of an anti-TNFα antibody (hereinafter referred to as "parent antibody" or "Ab-wt") were generated by introducing substitutions in the Fc region of the antibody amino acid sequence. The light chain of Ab-wt has the amino acid sequence as shown in SEQ ID NO:1, and the heavy chain of Ab-wt has the amino acid sequence as shown in SEQ ID NO:2. The mutations were introduced by site-directed mutagenesis by established methods. Briefly, mutations were introduced by PCR. The forward primer was designed to contain the intended mutation while the reverse primer was designed so that the 5' ends of the two primers anneal back-to-back (but do not overlap) (FIG. 9). PCR was run for 25 cycles (98° C. for 10 s, 64° C. for 30 s, 72° C. for 3 min). Before running the PCR product on an agarose gel, the non-mutated PCR template was removed from the pool of PCR products using the restriction enzyme DpnI. Following gel purification of the PCR product the blunt ends were ligated to obtain a circularized plasmid which was transformed into competent *E. coli* cells. Following overnight incubation several colonies were picked, the plasmid DNA isolated and sequenced to confirm that the mutation had been incorporated.

The non-fucosylated variants were generated by addition of 0.15 mM of the decoy substrate 2-deoxy-2-fluoro-2-fucose to the culture medium (Dekkers et al. (2016) Sci Rep 6:36964). This resulted in a significantly reduced incorporation of fucose in the IgG-Fc glycan, as shown in Example 11 hereinbelow.

TABLE 2

Generated antibody variants of an anti-TNFα antibody (EU numbering)

| Designation | Mutations relative to parent antibody |
|---|---|
| Ab-wt* | None (=parent antibody) |
| Ab-REW** | Q311R/M428E/N434W |
| Ab-REW-2FF** | non-fucosylated variant of Ab-REW |

*antibody not according to the invention;
**antibody according to the invention

Antibodies Ab-REW and Ab-REW-2FF are antibodies in accordance with the present invention.

Example 1. Affinity to TNFα

Method:

Affinity to TNFα was measured by Biacore. A CM5 chip was prepared using standard amine immobilisation Biacore procedures. Upon insertion of a CM5 chip the system was primed and then normalised with BIA-normalising solution (Biacore Preventative Maintenance Kit 2). The chip was added to the system with PBS-T running buffer; prior to immobilisation the chip surface was primed with three injections of 50 mM NaOH. Protein A was immobilised on the chip surface. For this, the protein was diluted to 5 μg/mL into 10 mM acetate buffer at pH 4.5 and injected so to generate a bound response of ~1000 RU's in all 4 flow cells. To remove non-covalently bound material from all the chip flow cells, three 15 second 50 mM NaOH washes were performed. On the Protein A chip, antibody was captured in flow cells 2 and 4, with flow cells 1 and 3 used for reference subtraction. The trial antibodies were diluted in PBS-T to 10 nM and 2.5-7.5 uL injected to obtain 120 RU of captured antibody. The analyte TNFα was prepared at 500 μg/mL in water as directed by the supplier and further diluted into the running buffer PBS-T. Single cycle kinetics was used to estimate the steady state affinity. For each single cycle analysis cycle a titration of 5 analyte concentrations were injected over the ligand and then the dissociation of the complex was measured. The surface was regenerated using glycine pH 1.7. A double referencing method was employed in which data from the ligand bound capture surface (fc 2 and 4) were subtracted from the references surfaces where no ligand was captured (fc 1 and 3 respectively). Blank injections of buffer were run every 3-4 cycles and then subtracted from analyte injection cycles, to correct for small changes in the ligand capture surface. Repeat injections of analyte at the start and end of each analytical run were used to check for sample degradation, or changes in the instrument performance. All analysis was performed at 25° C. and the sample rack was incubated at 10° C. during experimental runs. Each experiment was run at least three times. A 1-to-1 binding model was used to fit the resulting kinetic data.

Results:

All antibodies displayed similar binding kinetics to TNFα indicating that any introduced modification had not led to significant changes in the antigen binding region. For antibody Ab-REW-2FF the dissociation rate could not be measured, therefore affinity ($K_D$) could not be determined. However, the association rate was comparable to the other antibodies indicating that the introduction of the mutation does not affect the binding significantly.

TABLE 3

Binding kinetics of human IgG1 variants to TNFα as determined by SPR

|  | $k_a$ ($10^6$/Ms) | $k_d$ ($10^{-5}$/s) | $K_D$ (pM) |
|---|---|---|---|
| Ab-wt | 8.37 ± 0.11 | 3.45 ± 0.20 | 4.13 ± 0.19 |
| Ab-REW | 6.22 ± 0.91 | 2.04 ± 0.52 | 3.30 ± 0.74 |
| Ab-REW-2FF | 5.80 ± 0.58 | nd* | nd* |

*Dissociation rate (kd) could not be determined.

Example 2. Potency

Method:

L929 cells were incubated with 0.25 ng/mL of TNFα and 1 μg/well of actinomycin D in the presence of serial dilutions of anti-TNFα antibody variants. Following incubation for 20 h at 37° C./5% $CO_2$, the proliferative responses were measured using MTS (3-(4,5-dimethylthiazol-2-yl)-5-(3-carboxymethoxyphenyl)-2-(4-sulfophenyl)-2H-tetrazolium and an electron coupling reagent (phenazine ethosulfate, PES). MTS was converted into formazan product by dehydrogenase enzymes present in metabolically active cells. The quantity of formazan product as measured by absorbance at 492 nm was directly proportional to the number of living cells in culture.

Results:

The results are shown in FIG. 1. The introduction of mutations into the Fc region of the anti-TNFα antibody did not affect the potency.

Example 3. Affinity to Fcγ Receptors (CD64, CD32a, CD32b, CD16a, CD16b)

Method:

Affinity to FcγRs was measured by Biacore. A CM5 chip was prepared using standard amine immobilisation Biacore procedures. Upon insertion of a CM5 chip the system was primed and then normalised with BIA-normalizing solution (Biacore Preventative Maintenance Kit 2). The chip was added to the system with Phosphate Buffered Saline Tween-20 (PBS-T) running buffer; prior to immobilisation the chip surface was primed with three injections of 50 mM NaOH. FcγRs were immobilised on the chip surface using a His-tag capture system. The anti-His tag chip was prepared according to the Biacore kit instructions, with ~12000 RU's of the antibody deposited on all 4 flow cells. To remove non-covalently bound material from all the chip flow cells, three 30 second 10 mM glycine pH 1.5 washes were performed. The Fcγ receptors were diluted in PBS-T to a range of 0.5-2 μg/mL, with 2.5-5.0 μL injected onto the chip generating capture levels between 60 and 200 RU's. Antibodies were diluted into PBS-T prior to analysis. Single cycle kinetics were used to estimate the steady state affinity. For each single cycle analysis cycle a titration of 5 antibody concentrations were injected over the FcγR ligand and then the dissociation of the complex was measured. The surface was regenerated using the recommended solution, 10 mM glycine pH 1.5 for the anti-His capture surface. A double referencing method was employed in which data from the ligand bound capture surface (fc 2 and 4) were subtracted from the references surfaces where no ligand was captured (fc 1 and 3 respectively). Blank injections of buffer were run for every antibody titration cycle and then subtracted from analyte injection cycles, to correct for small changes in the ligand capture surface. All analysis was performed at 25° C. and the sample rack was incubated at 10° C. during experimental runs. Each experiment was run at least three times.

Results:

Binding to CD64 was not affected for the engineered anti-TNFα antibodies. The introduction of the mutations did not affect the affinity to CD32a(H), CD32a(R) and CD32b. However, Ab-REW-2FF showed a 5.5-fold increase in affinity to CD16a(V). The non-fucosylated antibody Ab-REW-2FF had also an improved binding to the low affinity CD16a receptor and to CD16b.

TABLE 4

Affinity to Fcγ receptors CD64, CD32a(H), CD32a(R) and CD32b as determined by SPR. The mean and standard deviation affinity calculated from two or more independent experiments is shown.

| | Affinity ($K_D$) | | | |
|---|---|---|---|---|
| | CD64 (nM) | CD32a(H) (μM) | CD32a(R) (μM) | CD32b (μM) |
| Ab-wt | 2.92 ± 0.07 | 0.67 ± 0.04 | nd | 3.14 ± 0.80 |
| Ab-REW | 2.80 ± 0.24 | 0.78 ± 0.05 | 1.60 ± 0.01 | 1.21 ± 0.32 |
| Ab-REW-2FF | 2.93 ± 0.16 | 1.87 ± 0.37 | 1.45 ± 0.01 | 1.13 ± 0.25 |

TABLE 5

Affinity to Fcγ receptors CD16a(V), CD16a(F) and CD16b as determined by SPR. The mean and standard deviation affinity calculated from two or more independent experiments is shown.

| | Affinity ($K_D$) | | |
|---|---|---|---|
| | CD16a(V) (nM) | CD16a(F) (μM) | CD16b(NA2) (μM) |
| Ab-wt | 184 ± 31.9 | nd | >3.00 |
| Ab-REW | 280 ± 36.1 | 2.41 ± 0.68 | 1.65 ± 0.36 |
| Ab-REW-2FF | 33.5 ± 0.99 | 0.15 ± 0.01 | 0.40 ± 0.07 |

Example 4. Affinity to FcRn

Method:

SPR was performed using a Biacore 3000 instrument with CM5 sensor chips coupled with anti-TNFα IgG1 antibodies (~500 resonance units (RU)) using amine-coupling chemistry as described by the manufacturer. The coupling was performed by injecting 2.0 ug/mL of each protein in 10 mM sodium acetate, pH 4.5, using the amine-coupling kit (GE Healthcare). HBS-P buffer pH 7.4 (10 mM HEPES, 150 mM NaCl, 0.005% surfactant P20) or phosphate buffer pH 6.0 (67 nM phosphate buffer, 150 mM NaCl, 0.005% Tween 20) were used as running and dilution buffer. Binding kinetics were determined by injecting titrated amounts (1000-31.2 nM) of monomeric His-tagged human FcRn (hFcRn) over immobilised antibodies at pH 7.4 or pH 6.0. All SPR experiments were conducted at 25° C. with a flow rate of 40 ul/min. Binding data were zero-adjusted, and reference cell value subtracted. The Langmuir 1:1 ligand binding model provided by the BIAevaluation software (version 4.1) was used to determine the binding kinetics.

Results:

The results showed that the wild-type antibody Ab-wt bound strictly pH dependently to hFcRn. All engineered antibody variants had a higher affinity to FcRn at pH 6.0, but kept their pH dependency and did not bind to the receptor at pH 7.4. Surprisingly, the REW containing variants showed >160-fold stronger binding at acidic pH and still no detectable binding under conditions tested at neutral pH. The antibody variants showed improved binding to FcRn compared to infliximab which contains a wildtype IgG1 Fc region.

TABLE 6

Affinity of anti-TNFα antibody variants
to FcRn at pH 6.0 and pH 7.4 as determined by SPR

| | pH 6.0 | | | pH 7.4 |
|---|---|---|---|---|
| | $K_D$ (nM) | Fold change from wt | Fold change from IFX | $K_D$ (nM) |
| Ab-wt | 1000 | | | NA |
| Ab-REW | 5.61 | 178 | 75.8 | NA |
| Ab-REW-2FF | 6.24 | 160 | 68.1 | NA |
| IFX | 425 | | | NA |

NA: not acquired due to weak binding.

Example 5. Transcytosis

Method:

Transwell filters (1.12 cm²) with collagen coated polytetrafluoroethylene (PTFE) membranes with 0.4 μm pore size were incubated O/N in complete growth medium followed by seeding of 1.0×10⁶ T84 cells per well. Transepithelial electrical resistance (TEER) was monitored daily using a MILLICELL-ERS-2 volt-ohm meter. The cultures were grown for 4-5 days before reaching confluence with a TEER value of ~1000-1300 Ω×cm². Prior to experiments the monolayers were starved for 1 h in Hank's Balanced Salt Solution (HBSS). Then, 400 nM of the the antibody variants or IFX alone or together with 4000 nM human myeloma IgG with irrelevant specificity were added to the apical Transwell chamber. Samples were collected from the basolateral reservoir at 0 and 4 h post adding. Antibody concentrations in the basolateral reservoir were determined by ELISA. Briefly, 96-well Maxisorp plates were coated O/N with either recombinant TNFα or an anti-human Fc specific antibody from goat, both diluted to 1 μg/ml in PBS. Subsequently, the plates were blocked with PBS containing 4% skimmed milk for 2 h at RT followed by washing 4 times with PBS containing 0.05% Tween 20. Samples collected during the transcytosis experiments were added to the wells and incubated for 2 h at RT before washing as above. Captured antibody variants, IFX or total IgG were detected using an alkaline phosphatase (ALP)-conjugated anti-human Fc specific antibody from goat. Binding was visualized by addition of 100 μl ALP-substrate and the 405 nm absorption spectrum was recorded. The amount of antibody variants, IFX and total IgG transported were calculated from standard curves of each of the individual antibody variants.

Transcytosis of Antibody Variants Across Polarized Human Epithelial Cells

Figure 2:
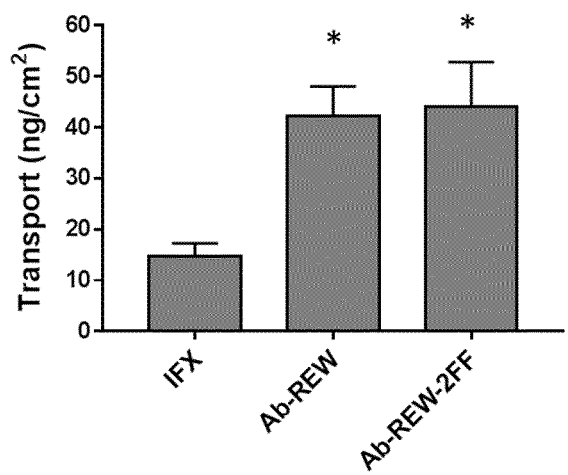
FIG. 2: Transport of anti-TNFα IgG variants across polarized T84 cells. The amounts of anti-TNFα antibody variants and Infliximab (IFX) from the apical to the basolateral reservoir at 4 hours post adding are shown. Presented as ng/cm$^2$. Error bars indicate SD of two to four individual monolayers.

Results:

The engineered anti-TNFα antibody variants were tested for transcytosis across a cell monolayer and compared to the wt antibody or IFX as another human IgG1 anti-TNFα antibody. The results are depicted in FIG. 2. The wt anti-TNFα antibody was transported from the apical to the basolateral reservoir. Compared to IFX, another IgG1 antibody with a wt Fc region, 2.8-fold more Ab-REW was transported which was also the case for Ab-REW-2FF.

Figure 3:
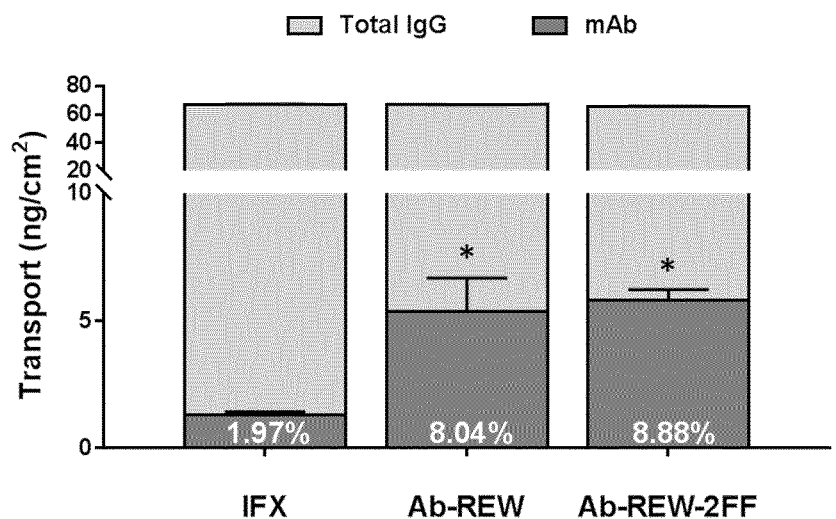
FIG. 3: Transport of anti-TNFα IgG variants across polarized T84 cells in the presence of excess amounts of myeloma IgG. The amounts of the anti-TNFα Ab variants and IFX transported from the apical to the basolateral reservoir in the presence of 10-fold excess of human myeloma IgG at 4 hours post adding are shown. Presented as ng/cm$^2$. Error bars indicate SD of three to four individual monolayers.

Transcytosis of Antibody Variants Across Polarized Human Epithelial Cells in the Presence of Competing IgG Results:

The total amount of immunoglobulin transported across a polarized T84 cell monolayer from the apical to the basolateral reservoir when the anti-TNFα antibody variants were incubated with a 10-fold excess of human myeloma IgG at 4 hours post adding was comparable for all antibodies. However, an increased affinity to FcRn at pH 6.0 resulted in a significantly higher percentage of specific anti-TNFα transport across the cell monolayer also in the presence of an excess of competing human IgG with irrelevant specificity. The results are depicted in FIG. 3.

Example 6. ADCC

Method:

An ADCC reporter bioassay core kit from Promega was used. Briefly, mTNFα CHO-K1 target cells at 1×10⁵/mL were seeded on white (clear bottom) tissue culture plates, 100 μL per well. The plates were incubated O/N at 37° C./5% $CO_2$. On day 2, 95 μL of assay medium was removed and replaced with 25 μL of engineered Jurkat effector cells at 3×10⁶/mL. The plates were then incubated for 6 h at 37° C./5% $CO_2$. The BioGlo™ reagent was prepared towards the end of the incubation. Plates were equilibrated to RT for 10-20 min before adding 75 μL of BioGlo™ reagent per well. After 5-10 min of incubation in the dark, luminescence was measured. A 4-PL model was used to fit the data.

Figure 4:
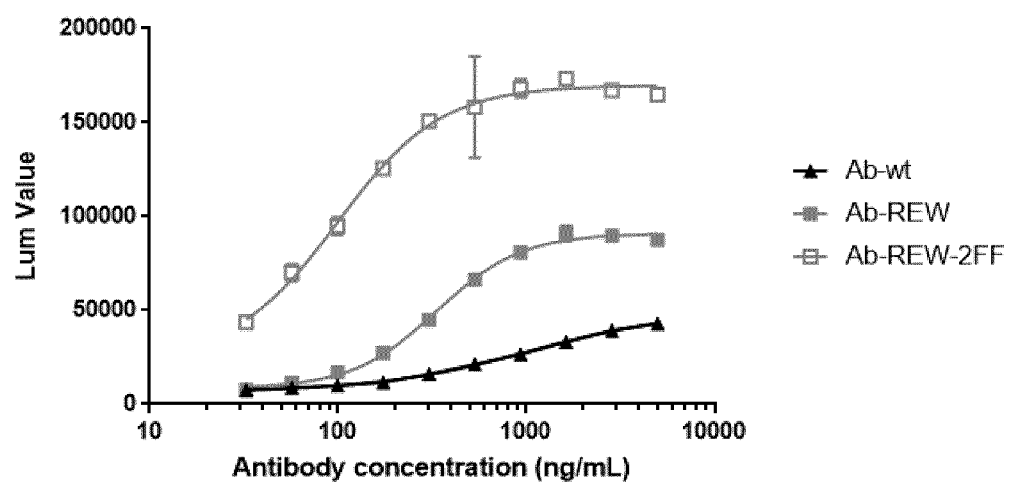
FIG. 4: ADCC activity. Induction of ADCC by anti-TNFα antibody variants, wild-type antibody and IFX.

Results:

The results (see FIG. 4) showed that all of the anti-TNFα antibodies induced ADCC but with distinct strengths. Compared to the wildtype antibody Ab-wt, the antibody variants showed increased ADCC. Specifically the non-fucosylated antibody variant Ab-REW-2FF had significantly improved ADCC.

Example 7. C1q Binding

Method:

ELISA was performed using 96-well MaxiSorp plates where the wells were coated with human TNFα diluted to 1 μg/mL in PBS. After incubation O/N at 4° C., the plates were blocked with PBS containing 4% skimmed milk for 1 h and washed four times with PBS containing 0.05% Tween-20 (PBS-T). Then, titrated amounts of the anti-TNFα IgG antibodies were diluted in PBS-T, added and incubated for 1 h at RT. After washing using PBS-T, human C1q (0.5 μg/mL) was diluted in 0.1 M Veronal buffer (0.25 mM $CaCl_2$ and 0.8 mM $MgCl_2$ pH 7.2), added to the wells and incubated for 1 h. Subsequently, the wells were washed as above before rabbit anti-human C1q diluted 1:5000 in PBS-T was added to the wells and incubated for 1 h. After washing, an HRP-conjugated anti-rabbit IgG from donkey diluted 1:5000 in PBS-T was added. Subsequently, the wells were washed and 100 μL 3,3',5,5'-Tetramethylbenzidine substrate was added to each well. The absorbance was measured at 620 nm using a Sunrise spectrophotometer.

Figure 5:
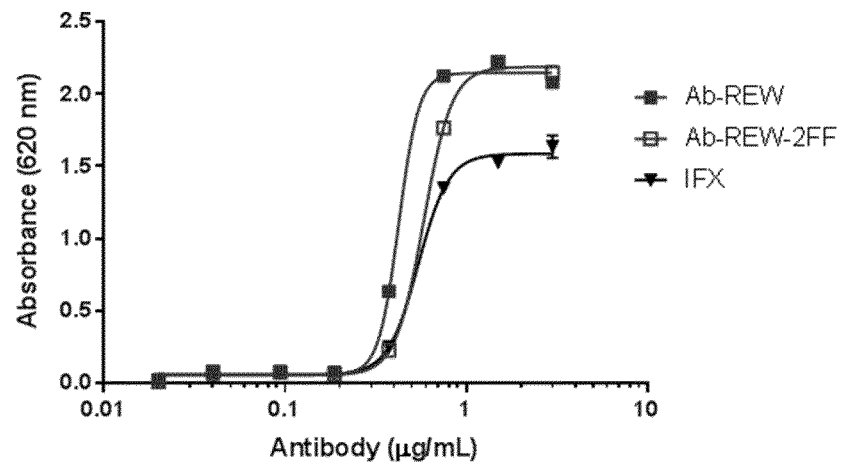
FIG. 5: Binding to human C1q. Binding of IFX and anti-TNFα antibody variants to human C1q. Each concentration was assayed in duplicate. Error bars indicate SD.

Results:

The anti-TNFα antibody variants were captured on human TNFα before human C1q was added. The results (see FIG. 5) showed that the antibodies bound C1q but with distinct binding strengths. Specifically, Ab-REW and Ab-REW-2FF bound somewhat stronger than IFX. The presence of fucose at the bi-antennary N-glucan attached to N297 had no or only a minor influence on binding. The binding hierarchy from strongest to weakest was as follows: Ab-REW>Ab-REW-2FF>IFX.

Example 8. CDC

Method:

The anti-TNFα CDC assay measured antibody dependent cytotoxicity of rabbit complement. Target cells expressing mTNFα were seeded into microplates in the presence of anti-TNFα antibodies that promoted the cytotoxic potential of complement. Six independent replicates of samples (anti-TNFα antibody variants) and 4 replicates of reference standard (IFX) were prepared at 60 µg/mL, serially diluted (1.3-fold dilution steps) and the dilution plates sealed until use. Target cells containing a LUC viability reporter were prepared to $1.5 \times 10^5$/mL and stored in a water bath at 37° C. Rabbit complement was diluted to 3-fold final assay concentration in DMEM High Glucose. Immediately after preparation, complement was combined with target cells in a 1:1 ratio (v/v). Forty µL of the complement/target cell preparation were transferred to each well of the assay plate. The antibodies prepared in the dilution plate were transferred to the cells (20 µL/well) and the plate was then incubated at 36° C./1% $CO_2$ for 3.5 h. Assay plates were equilibrated to RT in the dark for 35 min. Steady Glo which was equilibrated to ambient temperature for 120 min before use, was added to the assay plate (20 µL/well) and stored at RT in the dark for 35 min before luminescence was measured. Percent cell death was then calculated for each concentration of each sample and a 4-PL model was used to fit the data.

Figure 6:
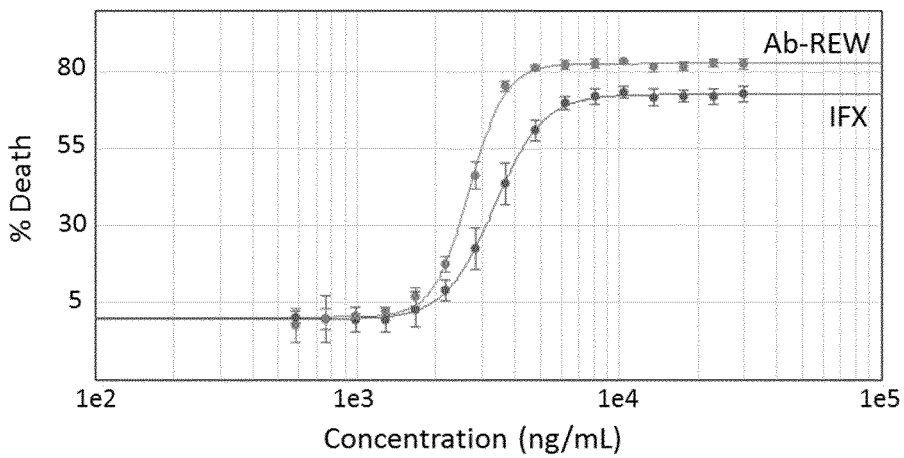
FIG. 6: CDC activity. Percent cell death for the various anti-TNFα variants compared to IFX. Each sample point is the mean of 6 independent replicates.
Figure 6:
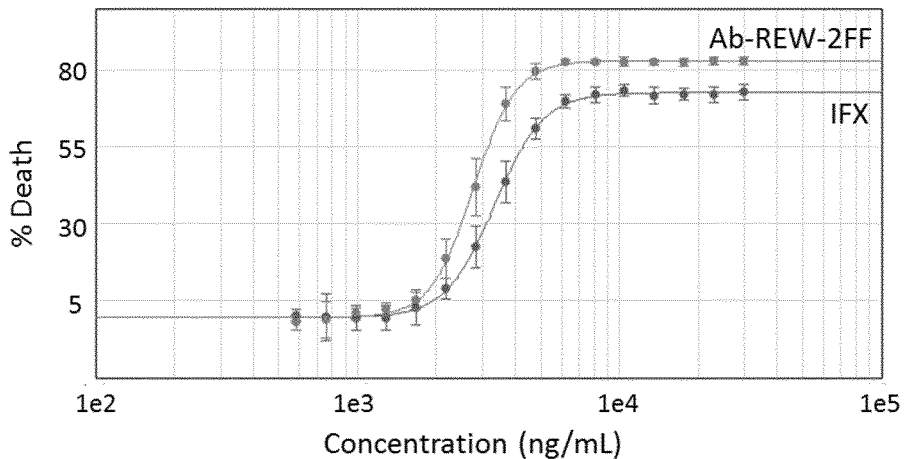

Results:

The results are shown in FIG. 6 and Table 7. The relative $EC_{50}$ and relative maximal % death results for test sample performance in the CDC assay provided a clear activity ranking that was consistent across both activity measures. Ab-REW showed greater CDC activity than IFX, irrespective of fucose content. In a direct comparison between fucose variant samples, to better understand the impact of fucose content on CDC activity, Ab-REW-2FF in comparison to Ab-REW, provided similar CDC activity responses. The comparison showed a relative $EC_{50}$ response of 97.1% and a relative maximal % death response of 100.4%.

TABLE 7

CDC activity of anti-TNFα antibody variants in terms of relative $EC_{50}$ and relative % death performance in comparison to IFX

| Sample ID | Relative EC50 (%) | Relative Maximal Death (%) |
|---|---|---|
| IFX | 100 | 100 |
| Ab-REW | 123.7 | 113.8 |
| Ab-REW-2FF | 120.1 | 114.2 |

Example 9. Induction of Regulatory Macrophages

Method:

Peripheral blood mononuclear cells (PBMC) were isolated from healthy buffy coats. Cells were isolated through Ficoll gradient centrifugation. Cells of two individual donors were mixed in equal numbers and $2 \times 10^5$ cells of the mixture were plated in 96 well plates in a total volume of 100 µL/well. Cells were incubated for 48 h at 37° C./5% $CO_2$. After 48 h, anti-TNFα antibody variants or IFX were added to reach a final concentration of 10 µg/mL. Each compound was added in replicates of five or six. Final volume was 150 µL/well. Human serum IgG1 (Sigma #15154) was used as control. After addition of the compounds, mixed lymphocyte reactions (MLRs) were cultured for another 4 days at 37° C./5% $CO_2$. Afterwards, plates were washed using PBS/5 mM EDTA (PBS/EDTA) and incubated with 50 µL/well PBS/EDTA for 20 min at RT. Plates were centrifuged and liquid was flicked out. Antibody was diluted in PBS/EDTA (anti-CD14-PE, anti-CD206-APC, both diluted 1:10). Cells were resuspended in 50 µL of antibody solution and incubated for 20 min at RT. Afterwards, cells were washed with PBS/EDTA and resuspended in 50 µL PBS/EDTA. Stained samples were analysed on a FACS Fortessa using FACSDiva software. Analysis was performed using FlowJo software.

Figure 7:
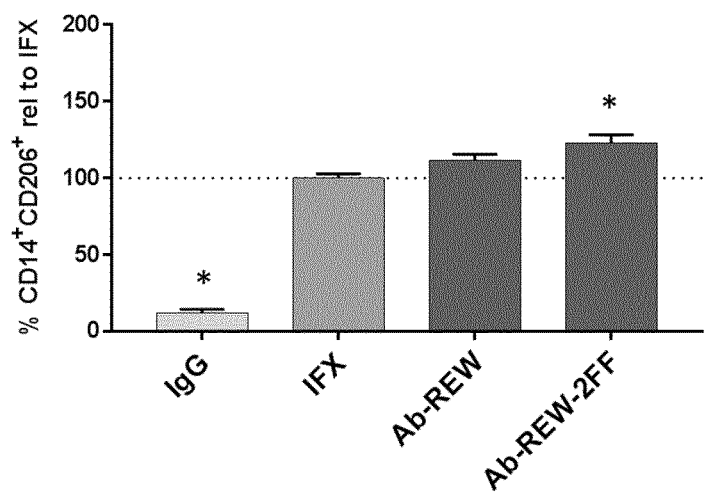
FIG. 7: Induction of CD14+CD206 macrophages by each compound relative to the induction of IFX. Summarized data of 4 independent experiments. Bars represent mean, error bars represent SEM.

Results:

Induction of regulatory macrophages was analysed in four independent MLRs and was successful in all experiments (comparing IFX to IgG control). The results are shown in FIG. 7. The levels of induction by IFX can differ between experiments due to the fact that each experiment was performed using different donors with inter-individual variation. All tested anti-TNFα antibody variants induced CD14+ CD206 regulatory macrophages with slight variation between the compounds. Ab-REW and Ab-REW-2FF induced slightly more regulatory macrophages than IFX, however, only in case of Ab-REW-2FF the increase was significant.

Example 10. Inhibition of T-Cell Proliferation

Method:

PBMC were isolated from healthy buffy coats. Cells were isolated through Ficoll gradient centrifugation. Cells of two individual donors were mixed in equal numbers and $2 \times 10^5$ cells of the mixture were plated in 96 well plates in a total volume of 100 µL/well. Cells were incubated for 48 h at 37° C./5% $CO_2$. After 48 h, anti-TNFα antibody variants or IFX were added to reach a final concentration of 10 µg/mL. Each compound was added in replicates of five or six. Final volume was 150 µL/well. Human serum IgG1 (Sigma #15154) was used as control. After addition of the compounds, mixed lymphocyte reactions (MLRs) were cultured for another 2 days at 37° C./5% $CO_2$. Afterwards, tritiated thymidine ($^3$H thymidine, 0.5 microCurie/well) was added to the cultures. Cultures were further incubated for 18 h at 37° C./5% $CO_2$. Samples were harvested using a Microbeta Filtermat 96 cell harvester and analysed using a Microbeta MicroplateCounter equipped with a single detector. Samples were counted for 10 seconds/well and converted to counts per minute (cpm).

Figure 8:
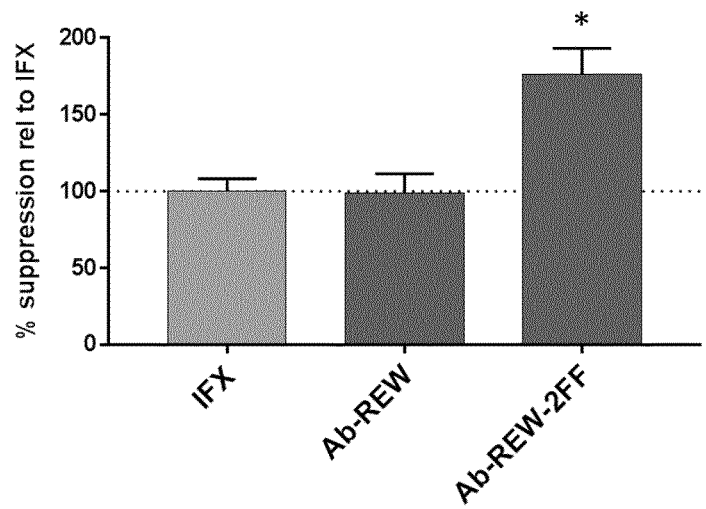
FIG. 8: Suppression of T-cell proliferation by each compound relative to IFX. Summarized data of 3 independent experiments. Bars represent mean, error bars represent SEM.

Results:

Inhibition of T-cell proliferation was measured in three independent MLRs and was defined as successful if IFX as positive control induced suppression. The levels of suppression by IFX in individual experiments can differ presumably due to the variance in regulatory macrophage induction. In each experiment, the potential of the anti-TNFα antibody variants to suppress T-cell proliferation was calculated relative to the positive control IFX. Antibody Ab-REW-2FF showed significantly enhanced suppression compared to IFX while suppression by Ab-REW was comparable to IFX (see FIG. 8).

Example 11. Analysis of N-Glycans

Method:

50 µl of each IgG variant (1 mg/ml) was spun down for 10 min at 13,000×g before 1 µg trypsin dissolved in 100 µl 50 mM ammonium bicarbonate (pH 7.8) was added and incubated overnight at 37° C. The centrifugal devices were spun down at 13,000×g for 10 min, and the flow-through was transferred to an Eppendorf tube and dried in a Speed-Vac (Heto Maxi dry). Dried samples were dissolved in 20 µl 1% formic acid, sonicated for 30 s, and centrifuged for 10 min at 16,100×g. Subsequently, each sample was transferred to new vials, and reverse phase (C18) nano online liquid chromatography-tandem mass spectrometry (LC-MS/MS) analysis of proteolytic peptides was performed using a Dionex Ultimate 3000 UHPLC systems (Thermo Fisher Scientific, USA). 5 µl of peptide solution was injected into the extraction column and peptides were eluted in the back-flush mode from the extraction column onto the analytical column. The mobile phase consists of acetonitrile and mass spectrometry grade water, both containing 0.1% formic acid. Chromatographic separation was achieved using a binary gradient from 3 to 50% of acetonitrile in water for 60 minutes with a flow rate of 0.3 µl/min. The LC system was coupled via a nanoelectrospray ion source to a Q exactive hybrid quadrupole orbitrap mass spectrometer (Thermo Fisher Scientific, USA). Peptide samples were analyzed with a high energy collisional dissociation (HCD) fragmentation method with normalized collision energy at 20, acquiring one Orbitrap survey scan in the mass range of m/z 300-2000 followed by MS/MS of the ten most intense ions in the Orbitrap.

Data analysis was performed on Xcalibur v2.0. MS/MS spectra for all N-glyco-peptides were extracted by oxonium ion search; 204.086 (N-acetylhexosamine) and 366.1388 (N-acetylhexosamine-hexose). By using HCD fragmentation with normalized collision energy at 20 the glycan structure and the peptide mass for IgG were detected. Extracted ion chromatograms for target glycol-peptides (EEQYNSTYR for IgG1) were extracted with 10 ppm accuracy and the corresponding MS/MS spectra were manually verified. HCD fragmentation with normalized collision energy at 35 was used to detect the peptide sequence and to verify that the peptide mass corresponded to the correct peptide sequence. The area under the curve for all extracted glycol-peptides was calculated and the percentage ratio for each glycoform was determined.

Figure 10:
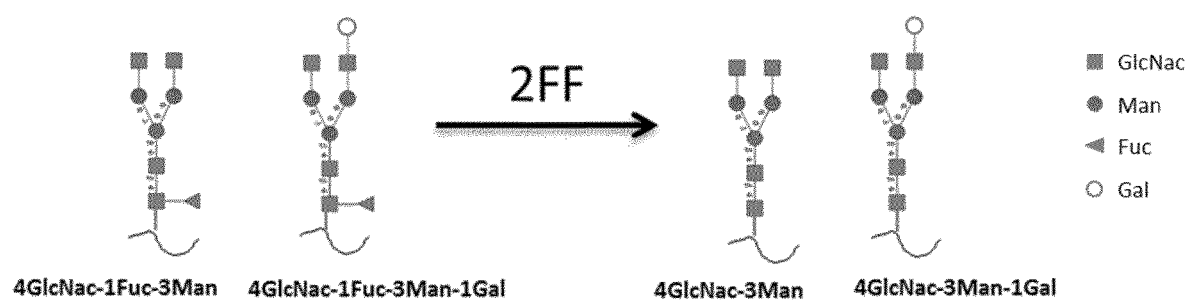
FIG. 10: A schematic illustration of the dominating N-glycan forms attached to N297 of the anti-TNFα antibody variants. The two N-glycan profiles that dominated among the panel of tested anti-TNFα antibody variants were 4GlcNac-1 Fuc-3Man and 4GlcNac-1 Fuc-3Man-1 Gal while for the IgG variants produced in the presence of 2FF the same bi-antennary structures occurred except that these lacked the fucose.

Results:

For Ab-REW two N-glycan forms dominated and corresponded to >90% of the total N-glycan pool, namely 4GlcNac-1Fuc-3Man and 4GlcNac-1Fuc-3Man-1 Gal. Both the N-glycan forms that dominated contained a core fucose. To produce the "non-fucosylated" version of Ab-REW (Ab-REW-2FF), the decoy substrate 2-deoxy-2-fluoro-1-fucose (2FF) was used. MS mapping of this antibody revealed that this strategy successfully resulted in greatly reduced incorporation of fucose, as a drop from >90% to 13% was detected. The dominating N-glycan forms after treatment were the same as the variants produced in the absence of 2FF, except that these structures lacked fucose (see also FIG. 10).

TABLE 8

Percentage of N-glycan forms attached to N297 of anti-TNFα IgG antibodies

| N-glycan structure | Ab-REW (%) | Ab-REW-2FF (%) |
|---|---|---|
| 4GlcNac-1Fuc-3Man | 69.1 | 8.5 |
| 4GlcNac-1Fuc-3Man-1Gal | 21.7 | 4.5 |
| 4GlcNac-3Man | 0.7 | 64.3 |
| 4GlcNac-3Man-1Gal | 0 | 17.3 |
| Other glycosylation patterns | 8.5 | 5.4 |

The invention claimed is:

1. An antibody comprising a TNFα-binding domain and an FcRn-binding site, wherein said antibody has a high affinity to human FcRn at pH 6, said high affinity being characterized by a dissociation equilibrium constant ($K_D$) of less than 100 nM, further wherein said antibody has no affinity or a low affinity to human FcRn at pH 7.4, said low affinity being characterized by a $K_D$ of greater than 10 μM, further wherein the amino acid sequence of the antibody comprises the amino acids 311R, 428E, and 434W, wherein the numbering of amino acid residues is according to the EU index, further wherein the antibody comprises (i) a $V_L$ domain comprising a CDR1 region having the amino acid sequence as shown in SEQ ID NO:3, a CDR2 region having the amino acid sequence as shown in SEQ ID NO:4, and a CDR3 region having the amino acid sequence as shown in SEQ ID NO:5, and (ii) a $V_H$ domain comprising a CDR1 region having the amino acid sequence as shown in SEQ ID NO:6, a CDR2 region having the amino acid sequence as shown in SEQ ID NO:7, and a CDR3 region having the amino acid sequence as shown in SEQ ID NO:8.

2. The antibody of claim 1, wherein said high affinity to human FcRn at pH 6 is characterized by a dissociation constant $K_D$ of less than 10 nM.

3. The antibody of claim 1, wherein said antibody binds to human TNFα with a $K_D$ of less than 100 pM.

4. The antibody of claim 1, wherein said antibody is a non-fucosylated antibody or an antibody having reduced fucosylation.

5. A pharmaceutical composition comprising the antibody according to claim 1 in combination with a pharmaceutically acceptable carrier.

* * * * *

SEQUENCE LISTING

<160> NUMBER OF SEQ ID NOS: 24

<210> SEQ ID NO 1
<211> LENGTH: 221
<212> TYPE: PRT
<213> ORGANISM: Artificial Sequence
<220> FEATURE:
<223> OTHER INFORMATION: Light chain of Ab-wt, the parent antibody of
      the modified antibodies used in the examples (clone 16-22-H05)

<400> SEQUENCE: 1

Asp Ile Gln Met Thr Gln Ser Pro Ser Ser Leu Ser Ala Ser Val Gly
1               5                   10                  15

Asp Arg Val Thr Ile Lys Cys Gln Ala Ser Gln Ser Ile Phe Ser Gly
            20                  25                  30

Leu Ala Trp Tyr Gln Gln Lys Pro Gly Lys Ala Pro Lys Leu Leu Ile
        35                  40                  45

Tyr Gly Ala Ser Lys Leu Ala Ser Gly Val Pro Ser Arg Phe Ser Gly
    50                  55                  60

Ser Gly Ser Gly Thr Glu Phe Thr Leu Thr Ile Ser Gly Leu Gln Pro
65                  70                  75                  80

Ala Asp Phe Ala Thr Tyr Tyr Cys Gln Ser Tyr Tyr Tyr Ser Ser Ser
                85                  90                  95

Ser Ser Asp Gly Ser Tyr Ala Phe Gly Gly Gly Thr Lys Leu Thr Val
            100                 105                 110

Leu Gly Arg Thr Val Ala Ala Pro Ser Val Phe Ile Phe Pro Pro Ser
        115                 120                 125

Asp Glu Gln Leu Lys Ser Gly Thr Ala Ser Val Val Cys Leu Leu Asn
    130                 135                 140

```
Asn Phe Tyr Pro Arg Glu Ala Lys Val Gln Trp Lys Val Asp Asn Ala
145                 150                 155                 160

Leu Gln Ser Gly Asn Ser Gln Glu Ser Val Thr Glu Gln Asp Ser Lys
            165                 170                 175

Asp Ser Thr Tyr Ser Leu Ser Ser Thr Leu Thr Leu Ser Lys Ala Asp
            180                 185                 190

Tyr Glu Lys His Lys Val Tyr Ala Cys Glu Val Thr His Gln Gly Leu
            195                 200                 205

Ser Ser Pro Val Thr Lys Ser Phe Asn Arg Gly Glu Cys
            210                 215                 220

<210> SEQ ID NO 2
<211> LENGTH: 452
<212> TYPE: PRT
<213> ORGANISM: Artificial Sequence
<220> FEATURE:
<223> OTHER INFORMATION: Heavy chain of Ab-wt, the parent antibody of
      the modified antibodies used in the examples (clone 16-22-H05)

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Lys Ala Ser Gly Ile Asp Phe Asn Asn Tyr
            20                  25                  30

Gly Ile Gly Trp Val Arg Gln Ala Pro Gly Lys Gly Leu Glu Trp Ile
        35                  40                  45

Thr Tyr Ile Tyr Pro Gly Phe Ala Ile Thr Asn Phe Ala Asn Ser Val
50                  55                  60

Lys Gly Arg Phe Thr Ile Ser Ser Asp Asn Ser Lys Asn Thr Val Tyr
65                  70                  75                  80

Leu Gln Met Asn Ser Leu Arg Ala Glu Asp Thr Ala Val Tyr Tyr Cys
            85                  90                  95

Ala Arg Asp Pro Val Tyr Ala Thr Ser Ser Gly Tyr Phe Asp Leu Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
        210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
```

```
                    275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
                340                 345                 350
Val Tyr Thr Leu Pro Pro Ser Arg Glu Glu Met Thr Lys Asn Gln Val
                355                 360                 365
Ser Leu Thr Cys Leu Val Lys Gly Phe Tyr Pro Ser Asp Ile Ala Val
        370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
                420                 425                 430
Met His Glu Ala Leu His Asn His Tyr Thr Gln Lys Ser Leu Ser Leu
            435                 440                 445
Ser Pro Gly Lys
        450

<210> SEQ ID NO 3
<211> LENGTH: 11
<212> TYPE: PRT
<213> ORGANISM: Artificial Sequence
<220> FEATURE:
<223> OTHER INFORMATION: CDR L1 of clone 16-22-H05?

<400> SEQUENCE: 3

Gln Ala Ser Gln Ser Ile Phe Ser Gly Leu Ala
1               5                   10

<210> SEQ ID NO 4
<211> LENGTH: 7
<212> TYPE: PRT
<213> ORGANISM: Artificial Sequence
<220> FEATURE:
<223> OTHER INFORMATION: CDR L2 of clone 16-22-H05

<400> SEQUENCE: 4

Gly Ala Ser Lys Leu Ala Ser
1               5

<210> SEQ ID NO 5
<211> LENGTH: 15
<212> TYPE: PRT
<213> ORGANISM: Artificial Sequence
<220> FEATURE:
<223> OTHER INFORMATION: CDR L3 of clone 16-22-H05

<400> SEQUENCE: 5

Gln Ser Tyr Tyr Tyr Ser Ser Ser Ser Asp Gly Ser Tyr Ala
1               5                   10                  15

<210> SEQ ID NO 6
<211> LENGTH: 10
<212> TYPE: PRT
<213> ORGANISM: Artificial Sequence
```

```
<220> FEATURE:
<223> OTHER INFORMATION: CDR H1 of clone 16-22-H05

<400> SEQUENCE: 6

Gly Ile Asp Phe Asn Asn Tyr Gly Ile Gly
1               5                   10

<210> SEQ ID NO 7
<211> LENGTH: 17
<212> TYPE: PRT
<213> ORGANISM: Artificial Sequence
<220> FEATURE:
<223> OTHER INFORMATION: CDR H2 of clone 16-22-H05

<400> SEQUENCE: 7

Tyr Ile Tyr Pro Gly Phe Ala Ile Thr Asn Phe Ala Asn Ser Val Lys
1               5                   10                  15

Gly

<210> SEQ ID NO 8
<211> LENGTH: 13
<212> TYPE: PRT
<213> ORGANISM: Artificial Sequence
<220> FEATURE:
<223> OTHER INFORMATION: CDR H3 of clone 16-22-H05

<400> SEQUENCE: 8

Asp Pro Val Tyr Ala Thr Ser Ser Gly Tyr Phe Asp Leu
1               5                   10

<210> SEQ ID NO 9
<211> LENGTH: 122
<212> TYPE: PRT
<213> ORGANISM: Artificial Sequence
<220> FEATURE:
<223> OTHER INFORMATION: VH of humanized IgG of clone 16-22-H05

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Lys Ala Ser Gly Ile Asp Phe Asn Asn Tyr
            20                  25                  30

Gly Ile Gly Trp Val Arg Gln Ala Pro Gly Lys Gly Leu Glu Trp Ile
        35                  40                  45

Thr Tyr Ile Tyr Pro Gly Phe Ala Ile Thr Asn Phe Ala Asn Ser Val
    50                  55                  60

Lys Gly Arg Phe Thr Ile Ser Ser Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Asp Pro Val Tyr Ala Thr Ser Ser Gly Tyr Phe Asp Leu Trp
            100                 105                 110

Gly Gln Gly Thr Leu Val Thr Val Ser Ser
        115                 120

<210> SEQ ID NO 10
<211> LENGTH: 114
<212> TYPE: PRT
<213> ORGANISM: Artificial Sequence
<220> FEATURE:
<223> OTHER INFORMATION: VL of humanized IgG of clone 16-22-H05 ?

<400> SEQUENCE: 10
```

```
Asp Ile Gln Met Thr Gln Ser Pro Ser Ser Leu Ser Ala Ser Val Gly
1               5                   10                  15

Asp Arg Val Thr Ile Lys Cys Gln Ala Ser Gln Ser Ile Phe Ser Gly
            20                  25                  30

Leu Ala Trp Tyr Gln Gln Lys Pro Gly Lys Ala Pro Lys Leu Leu Ile
        35                  40                  45

Tyr Gly Ala Ser Lys Leu Ala Ser Gly Val Pro Ser Arg Phe Ser Gly
50                      55                  60

Ser Gly Ser Gly Thr Glu Phe Thr Leu Thr Ile Ser Gly Leu Gln Pro
65                  70                  75                  80

Ala Asp Phe Ala Thr Tyr Tyr Cys Gln Ser Tyr Tyr Ser Ser Ser
                85                  90                  95

Ser Ser Asp Gly Ser Tyr Ala Phe Gly Gly Gly Thr Lys Leu Thr Val
            100                 105                 110

Leu Gly
```

<210> SEQ ID NO 11
<211> LENGTH: 452
<212> TYPE: PRT
<213> ORGANISM: Artificial Sequence
<220> FEATURE:
<223> OTHER INFORMATION: Heavy chain of Ab-REW (based on clone 16-22-H05)

<400> SEQUENCE: 11

```
Glu Val Gln Leu Val Glu Ser Gly Gly Gly Leu Val Gln Pro Gly Gly
1               5                   10                  15

Ser Leu Arg Leu Ser Cys Lys Ala Ser Gly Ile Asp Phe Asn Asn Tyr
            20                  25                  30

Gly Ile Gly Trp Val Arg Gln Ala Pro Gly Lys Gly Leu Glu Trp Ile
        35                  40                  45

Thr Tyr Ile Tyr Pro Gly Phe Ala Ile Thr Asn Phe Ala Asn Ser Val
50                      55                  60

Lys Gly Arg Phe Thr Ile Ser Ser Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Asp Pro Val Tyr Ala Thr Ser Ser Gly Tyr Phe Asp Leu Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
130                     135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
210                     215                 220

Cys Asp Lys Thr His Thr Cys Pro Pro Cys Pro Ala Pro Glu Leu Leu
225                 230                 235                 240
```

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Arg Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Glu His Glu Ala Leu His Trp His Tyr Thr Gln Lys Ser Leu Ser Leu
        435                 440                 445

Ser Pro Gly Lys
    450

<210> SEQ ID NO 12
<211> LENGTH: 454
<212> TYPE: PRT
<213> ORGANISM: Artificial Sequence
<220> FEATURE:
<223> OTHER INFORMATION: Heavy chain of Ab-REW (based on clone 17-22-
    B03)

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Lys Ala Ser Gly Ile Asp Phe Ser Ala Gly
            20                  25                  30

Tyr Asp Met Cys Trp Val Arg Gln Ala Pro Gly Lys Gly Leu Glu Trp
        35                  40                  45

Ile Ala Cys Ile Asp Ser Arg Arg Glu Glu Ser Asp Tyr Ala Ser Trp
    50                  55                  60

Ala Lys Gly Arg Phe Thr Ile Ser Lys Asp Ser Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Gly Gly Tyr Gly Asp Gly Val Asp Gly Ala Phe Asp
            100                 105                 110

Pro Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly

```
                130             135             140
Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Gln Thr Tyr Ile Cys Asn
                195                 200                 205

Val Asn His Lys Pro Ser Asn Thr Lys Val Asp Lys Lys Val Glu Pro
            210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Arg Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Glu His Glu Ala Leu His Trp His Tyr Thr Gln Lys Ser Leu
            435                 440                 445

Ser Leu Ser Pro Gly Lys
            450

<210> SEQ ID NO 13
<211> LENGTH: 232
<212> TYPE: PRT
<213> ORGANISM: Artificial Sequence
<220> FEATURE:
<223> OTHER INFORMATION: Fc region of Ab-REW (including hinge region)

<400> SEQUENCE: 13

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
```

```
                    35                  40                  45
Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Arg
                     85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Glu His Glu Ala Leu His Trp His Tyr Thr Gln Lys
    210                 215                 220

Ser Leu Ser Leu Ser Pro Gly Lys
225                 230

<210> SEQ ID NO 14
<211> LENGTH: 11
<212> TYPE: PRT
<213> ORGANISM: Artificial Sequence
<220> FEATURE:
<223> OTHER INFORMATION: CDR L1 of clone 17-22-B03

<400> SEQUENCE: 14

Gln Ala Ser Gln Ser Ile Ser Ser Tyr Leu Ala
 1               5                  10

<210> SEQ ID NO 15
<211> LENGTH: 7
<212> TYPE: PRT
<213> ORGANISM: Artificial Sequence
<220> FEATURE:
<223> OTHER INFORMATION: CDR L2 of clone 17-22-B03

<400> SEQUENCE: 15

Lys Ala Ser Thr Leu Ala Ser
 1               5

<210> SEQ ID NO 16
<211> LENGTH: 13
<212> TYPE: PRT
<213> ORGANISM: Artificial Sequence
<220> FEATURE:
<223> OTHER INFORMATION: CDR L3 of clone 17-22-B03

<400> SEQUENCE: 16

Gln Cys Thr Tyr Tyr Glu Pro Ser Tyr Val Phe Arg Ala
 1               5                  10

<210> SEQ ID NO 17
```

```
<211> LENGTH: 11
<212> TYPE: PRT
<213> ORGANISM: Artificial Sequence
<220> FEATURE:
<223> OTHER INFORMATION: CDR H1 of clone 17-22-B03

<400> SEQUENCE: 17

Gly Ile Asp Phe Ser Ala Gly Tyr Asp Met Cys
1               5                   10

<210> SEQ ID NO 18
<211> LENGTH: 17
<212> TYPE: PRT
<213> ORGANISM: Artificial Sequence
<220> FEATURE:
<223> OTHER INFORMATION: CDR H2 of clone 17-22-B03

<400> SEQUENCE: 18

Cys Ile Asp Ser Arg Arg Glu Glu Ser Asp Tyr Ala Ser Trp Ala Lys
1               5                   10                  15

Gly

<210> SEQ ID NO 19
<211> LENGTH: 14
<212> TYPE: PRT
<213> ORGANISM: Artificial Sequence
<220> FEATURE:
<223> OTHER INFORMATION: CDR H3 of clone 17-22-B03

<400> SEQUENCE: 19

Gly Gly Tyr Gly Gly Asp Gly Val Asp Gly Ala Phe Asp Pro
1               5                   10

<210> SEQ ID NO 20
<211> LENGTH: 124
<212> TYPE: PRT
<213> ORGANISM: Artificial Sequence
<220> FEATURE:
<223> OTHER INFORMATION: VH of humanized IgG of clone 17-22-B03

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Lys Ala Ser Gly Ile Asp Phe Ser Ala Gly
            20                  25                  30

Tyr Asp Met Cys Trp Val Arg Gln Ala Pro Gly Lys Gly Leu Glu Trp
        35                  40                  45

Ile Ala Cys Ile Asp Ser Arg Arg Glu Glu Ser Asp Tyr Ala Ser Trp
    50                  55                  60

Ala Lys Gly Arg Phe Thr Ile Ser Lys Asp Ser Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Gly Gly Tyr Gly Gly Asp Gly Val Asp Gly Ala Phe Asp
            100                 105                 110

Pro Trp Gly Gln Gly Thr Leu Val Thr Val Ser Ser
        115                 120

<210> SEQ ID NO 21
<211> LENGTH: 112
<212> TYPE: PRT
<213> ORGANISM: Artificial Sequence
<220> FEATURE:
```

<223> OTHER INFORMATION: VL of humanized IgG of clone 17-22-B03?-(sc08)

<400> SEQUENCE: 21

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Cys Thr Tyr Tyr Glu Pro Ser
                85                  90                  95

Tyr Val Phe Arg Ala Phe Gly Gly Gly Thr Lys Leu Thr Val Leu Gly
            100                 105                 110
```

<210> SEQ ID NO 22
<211> LENGTH: 112
<212> TYPE: PRT
<213> ORGANISM: Artificial Sequence
<220> FEATURE:
<223> OTHER INFORMATION: VL of humanized IgG of clone 17-22-B03?-(sc02)

<400> SEQUENCE: 22

```
Asp Ile Gln Met Thr Gln Ser Pro Ser Ser Leu Ser Ala Ser Val Gly
1               5                   10                  15

Asp Arg Val Thr Ile Lys Cys Gln Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Asp Leu Glu Pro
65                  70                  75                  80

Ala Asp Phe Ala Thr Tyr Tyr Cys Gln Cys Thr Tyr Tyr Glu Pro Ser
                85                  90                  95

Tyr Val Phe Arg Ala Phe Gly Gly Gly Thr Lys Leu Thr Val Leu Gly
            100                 105                 110
```

<210> SEQ ID NO 23
<211> LENGTH: 219
<212> TYPE: PRT
<213> ORGANISM: Artificial Sequence
<220> FEATURE:
<223> OTHER INFORMATION: Light chain of humanized IgG of clone 17-22-
    B03?-(sc08)

<400> SEQUENCE: 23

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Cys Thr Tyr Tyr Glu Pro Ser
                85                  90                  95

Tyr Val Phe Arg Ala Phe Gly Gly Gly Thr Lys Leu Thr Val Leu Gly
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 24
<211> LENGTH: 219
<212> TYPE: PRT
<213> ORGANISM: Artificial Sequence
<220> FEATURE:
<223> OTHER INFORMATION: Light chain of humanized IgG of clone 17-22-
      B03?-(sc02)

<400> SEQUENCE: 24

Asp Ile Gln Met Thr Gln Ser Pro Ser Ser Leu Ser Ala Ser Val Gly
1               5                   10                  15

Asp Arg Val Thr Ile Lys Cys Gln Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Asp Leu Glu Pro
65                  70                  75                  80

Ala Asp Phe Ala Thr Tyr Tyr Cys Gln Cys Thr Tyr Tyr Glu Pro Ser
                85                  90                  95

Tyr Val Phe Arg Ala Phe Gly Gly Gly Thr Lys Leu Thr Val Leu Gly
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

```
Ser Gly Asn Ser Gln Glu Ser Val Thr Glu Gln Asp Ser Lys Asp Ser
                165             170             175

Thr Tyr Ser Leu Ser Ser Thr Leu Thr Leu Ser Lys Ala Asp Tyr Glu
            180             185             190

Lys His Lys Val Tyr Ala Cys Glu Val Thr His Gln Gly Leu Ser Ser
        195             200             205

Pro Val Thr Lys Ser Phe Asn Arg Gly Glu Cys
    210             215
```